US00RE35474E

United States Patent [19]

Woodard et al.

[11] E Patent Number: Re. 35,474

[45] Reissued Date of Patent: Mar. 11, 1997

[54] TRANSDERMAL DRUG DELIVERY DEVICES WITH AMINE-RESISTANT SILICONE ADHESIVES

[75] Inventors: John T. Woodard, Midland; Virgil L. Metevia, Saginaw, both of Mich.

[73] Assignee: Dow Corning Corporation, Midland, Mich.

[21] Appl. No.: 322,975

[22] Filed: Oct. 13, 1994

Related U.S. Patent Documents

Reissue of:

[64] Patent No.: 4,655,767
Issued: Apr. 7, 1987
Appl. No.: 780,505
Filed: Sep. 26, 1985

U.S. Applications:

[63] Continuation-in-part of Ser. No. 665,803, Oct. 29, 1984, abandoned.

[51] Int. Cl.[6] ..... A61F 13/02; A61L 15/00

[52] U.S. Cl. ..... 424/448; 424/449; 428/156; 604/890.1

[58] Field of Search ..... 604/890.1; 424/448, 424/449; 428/156

[56] References Cited

U.S. PATENT DOCUMENTS

| | | | |
|---|---|---|---|
| 2,736,721 | 2/1956 | Dexter | 260/42 |
| 2,814,601 | 11/1957 | Currie et al. | 260/29.1 |
| 2,857,356 | 10/1958 | Goodwin | 260/42 |
| 3,528,940 | 9/1970 | Modic | 260/37 |
| 3,731,683 | 5/1973 | Zaffaroni | 128/268 |
| 3,797,494 | 3/1974 | Zaffaroni | 128/268 |
| 3,929,704 | 12/1975 | Horning | 260/29.1 SB |
| 3,983,298 | 9/1976 | Hahn et al. | 428/355 |
| 4,031,894 | 6/1977 | Urguhart et al. | 128/268 |
| 4,255,316 | 3/1981 | Blizzard | 260/37 SB |
| 4,309,520 | 1/1982 | Blizzard | 525/477 |
| 4,336,243 | 6/1982 | Sanvordeker et al. | 424/28 |
| 4,417,042 | 11/1983 | Dziark | 528/18 |
| 4,460,371 | 7/1984 | Abber | 604/897 |
| 4,588,580 | 5/1986 | Gale et al. | 424/21 |

FOREIGN PATENT DOCUMENTS

| | | |
|---|---|---|
| 575664 | 5/1959 | Canada . |
| 859511 | 1/1961 | Canada . |
| 711756 | 6/1965 | Canada . |
| 5923293 | 7/1981 | Japan . |
| 859511 | 1/1961 | United Kingdom . |

OTHER PUBLICATIONS

One page memo "To: All Adhesives Customers" From: S. Michael John, Silicone Products Division, General Electric Company Waterford, NY dated Aug. 1983 containing the following data sheets (2 pages each): CDS–4131, SRC 18, PSA 518, PSA 529, PSA 590, PSA 595, PSA 596, PSA 6573, PSA 6574, CDS–4138.

Chemical Abstracts, vol. 88, 1978, pp55, Abstract No. 88:122452m Poly(organosiloxanes). Karlin, A. V.; Lobkov, V. D.; Andrianov, K. A.; Petrova, I. M.; Vasil'eva, N. A.; Trofimov, V. M.; U.S.S.R.

*Primary Examiner*—Ralph H. Dean
*Attorney, Agent, or Firm*—Sharon K. Severance

[57] ABSTRACT

This invention relates to an improved transdermal drug delivery device for the controlled transdermal delivery of amino-functional drugs. The improvement resides in providing the device with a silicone pressure-sensitive adhesive layer which has been chemically treated to reduce the silicon-bonded hydroxyl content of the pressure-sensitive adhesive composition to render the adhesive layer resistant to loss of tack and preserve the instant adherence of the device to the skin of a wearer during storage and while the device is being worn. Preferably, the composition used comprises a silicon-bonded hydroxyl radical containing resinous copolymer of $R_3SiO_{1/2}$ units and $SiO_{4/2}$ units and a polydiorganosiloxane which have been chemically treated with $R_3SiO_{1/2}$ units where R is preferably a hydrocarbon radical such as a methyl group to reduce the silicon-bonded hydroxyl content of the adhesive and thereby its sensitivity to amino-functional drugs.

52 Claims, 2 Drawing Sheets

TRANSDERMAL DRUG DELIVERY DEVICES WITH AMINE-RESISTANT SILICONE ADHESIVES

Matter enclosed in heavy brackets [ ] appears in the original patent but forms no part of this reissue specification; matter printed in italics indicates the additions made by reissue.

BACKGROUND OF THE INVENTION

This application is a continuation-in-part of U.S. Ser. No. 06/665,803, filed on Oct. 29, 1984, now abandoned.

This invention relates to a transdermal drug delivery device for the controlled release of an amino-functional drug which contains a silicone skin contact pressure-sensitive adhesive layer made from an adhesive composition which has been chemically treated to render the adhesive more resistant to the loss of tack and thus the ability to instantly adhere to the skin caused by amino-functional drugs such as propranolol.

Transdermal drug delivery devices for the continuous controlled transdermal administration of a drug are an attractive and convenient alternative to other means of drug delivery such as by ingesting medication at fixed time intervals orally or by way of a subcutaneous injection. Examples of such devices can be found in U.S. Pat. Nos. 3,731,683 (Zaffaroni); 3,797,494 (Zaffaroni); 4,031,894 (Uhrquhart, et al.) and 4,336,243 (Sanvordeker, et al.). Such devices are held in contact with the skin by means of a pressure-sensitive adhesive layer and the devices are typically intended to be left in contact with the skin for a period of 24 hours or more. In view of the extended period of contact with the skin, the adhesive layer should be capable of adhering to the skin for at least that length of time and should also be reasonably non-irritating and non-sensitizing to the skin.

Silicone pressure-sensitive adhesives are known to be non-irritating and non-sensitizing to the skin and have been used as adhesive layers for certain such devices such as those for the controlled release of nitroglycerine. One example of a medical grade of silicone pressure-sensitive is DOW CORNING® 355 Medical Grade Adhesive which is commercially available from Dow Corning Corporation, Midland, Mich. 48640.

The known advantages of continuous transdermal drug delivery devices has prompted efforts to develop transdermal drug delivery systems for delivery of other drugs. One such system which has been developed is one for the delivery of scopolamine which uses an polyisobutylene pressure-sensitive adhesive layer. Organic polymer-based adhesives such as acrylic adhesives are known to cause skin sensitization in some individuals and manufacturers of devices having organic pressure-sensitive adhesives commonly recommend that such devices be applied to different places on the skin when such devices are to be worn for extended periods of time to avoid skin sensitization. Some persons may require use of such devices for long periods of time.

In seeking to develop transdermal drug delivery systems for various types of drugs which employ a silicone pressure-sensitive adhesive layer, we became aware of the fact that certain drugs tend to cause the adhesive layer to lose its tack and thereby lose its ability to adhere the device to the skin. As is well known, a releasable backing layer is typically placed over the pressure-sensitive adhesive layer to protect the adhesive layer from loss of tack due to dirt and other contaminants during storage and due to handling prior to application. Since the silicone pressure-sensitive adhesive layer is permeable to drugs, the drug permeates through the adhesive layer to the backing and is therefore in contact with the adhesive layer during storage.

We have observed that exposure to amines and amino-functional drugs tends to cause certain silicone pressure-sensitive adhesives to lose tack and thus lose their ability to instantly adhere to the skin. Once tack was lost, a considerable amount of pressure is needed to obtain adherence to the skin and this is undesirable from the standpoint of the wearer. This change was further evidenced by the observation that addition of an amine to a silicone pressure-sensitive adhesive composition having a low tack value and a relatively high level of the hereinafter described silicone copolymer resin often caused the viscosity of the composition to increase with time and even to gel.

SUMMARY OF THE INVENTION

It is the object of this invention to provide an improved transdermal drug delivery device for the controlled transdermal drug delivery of an amino-functional drug which is held to the skin of a wearer by means of a biocompatible silicone pressure-sensitive adhesive layer whose tack and instant adhesion properties are relatively unaffected by contact with the amino-functional drug.

This and other objects are provided by a method of making such a device by placing a biocompatible silicone pressure-sensitive adhesive layer on the skin contact portions of the device wherein the silicone pressure-sensitive adhesive composition employed is one which comprises a combination of a resinous copolymer consisting essentially of triorganosiloxy units and tetrafunctional siloxy units in a ratio of about 0.6 to 0.9 triorganosiloxy units for each tetrafunctional siloxy unit present in the copolymer and a polydiorganosiloxane. The improvement resides in the use of such a silicone pressure-sensitive adhesive composition which has been chemically treated to reduce the silicon-bonded hydroxyl content of the adhesive composition from what it would have originally been without such treatment to a sufficient extent that the adhesive is rendered more resistant to loss of tack caused by exposure to the amino-functional drug, particularly a drug having a pKa of greater than about 8.5, than an untreated composition. In a preferred embodiment, the adhesive layer is obtained from a silicone pressure-sensitive composition which is chemically treated by reacting the silicon-bonded hydroxyl radicals with from 0.8 to 3 moles of triorganosiloxy units per mole of silicon-bonded hydroxyl radicals where the triorganosiloxy units are derived from an organosilazane such as hexamethyldisilazane.

BRIEF DESCRIPTION OF THE DRAWINGS

The above and other objects, features and advantages of the present invention will become apparent to those skilled in the art upon an examination of the following description and drawing which are merely illustrative of the present invention. In the Drawings.

DETAILED DESCRIPTION OF THE INVENTION

Figure 1:
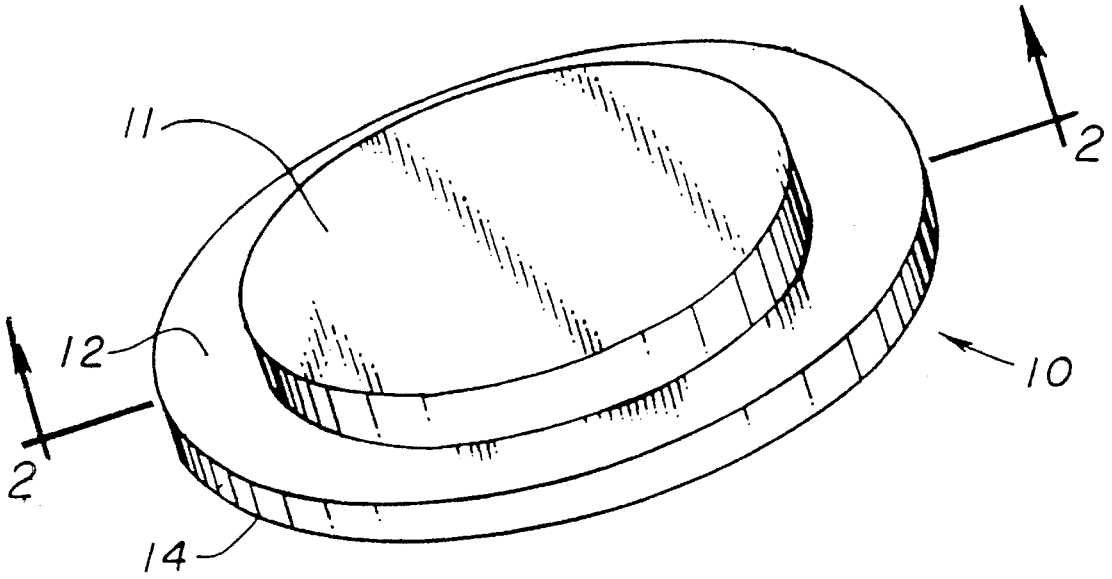
FIG. 1 is a perspective view of one embodiment of a transdermal drug delivery device 10.

Referring to the Drawings, FIG. 1 shows one embodiment of a transdermal drug delivery device 10 useful in the present invention shown as raised portion 11 surrounded by and integral with rim 12 and contains a backing material 14 on the side of device 10 which is intended to be positioned against the wearer's skin. Raised portion 11 and rim 12 can be made of any suitable polymeric material which is preferably not permeable to the drug being delivered such as aluminum foil and impermeable organic polymers.

Figure 2:
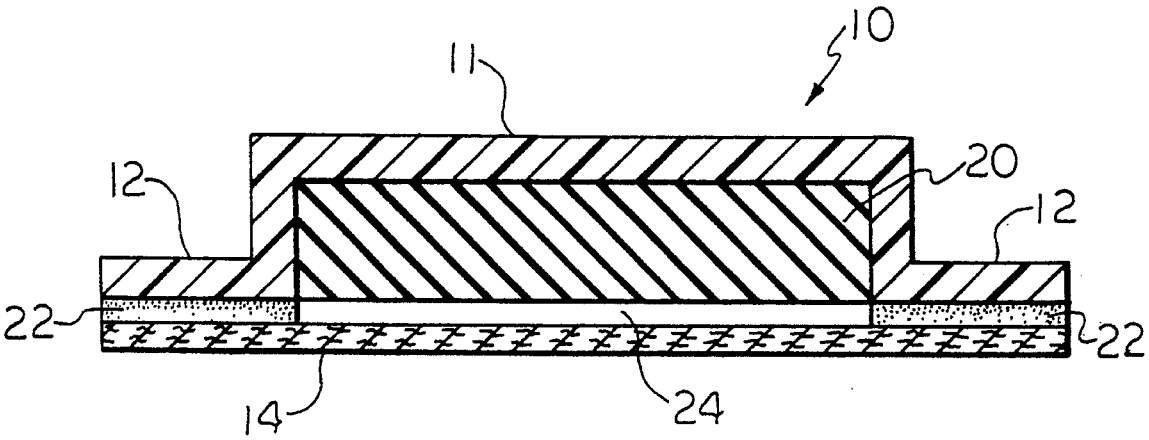
FIG. 2 is a cross-section of FIG. 1 taken along section line 2—2.

Referring to FIG. 2, raised portion 11 forms a cavity in which a means for holding and controllably releasing the drug to be delivered is placed. FIG. 2 shows one example of such a means as an elastomeric body 20 impregnated with a drug such as scopolamine. When backing material 14 which is a conventional drug impermeable film coated with a conventional release coating for silicone pressure-sensitive adhesives is removed, device 10 is adhered to the wearer's skin by pressing the device against the skin to permit it to contact silicone pressure-sensitive adhesive layer 22.

Once in contact with the skin the drug permeates from elastomeric body 20 (which can be a silicone elastomer which is permeable to the amino-functional drug to be delivered) in a controlled manner into space 24 and thereby comes in contact with the wearer's skin and transdermally enters the body. Space 24 can be a continuation of adhesive layer 22 such that the entire skin contact surface of device 10 is coated with adhesive to improve contact with the skin and the drug is allowed to permeate through the adhesive layer before reaching the skin. It is therefore apparent that the amino-functional drug can intimately contact the silicone-pressure sensitive adhesive.

As is well known to those skilled in the art, other types of drug reservoirs can be used to manufacture transdermal drug delivery devices and with the exception of the use of an amino-functional drug in combination with silicone pressure-sensitive adhesive layers as will be described in more detail, infra, the form and means by which such drugs are delivered form no part of the present invention. For example, elastomeric body 20 could be replaced by a solution of the amino-functional drug to be delivered and space 24 could comprise a semipermeable membrane which controls the release rate of the drug to the skin. The aforementioned patents to Zaffaroni, Uhrquhart, et al. and Sandvordeker, et al. describe other types of transdermal drug delivery devices employing pressure-sensitive adhesive layers and are hereby incorporated by reference to teach other examples of transdermal drug delivery devices which may find use in the present invention.

More specifically, this invention relates to an improved transdermal drug delivery device for the controlled transdermal delivery of a drug comprising a container having a controlled drug delivery means associated therewith, said container being adapted to hold said drug delivery means in close proximity to the skin of a wearer, said device having a biocompatible silicone pressure-sensitive adhesive layer thereon for maintaining contact between said container and the skin of a wearer, said layer being deposited from a silicone pressure-sensitive adhesive composition containing silicon-bonded hydroxyl radicals which comprise a combination of (A) a resinous copolymer consisting essentially of triorganosiloxy units and tetrafunctional siloxy units in a ratio of about 0.6 to 0.9 triorganosiloxy units for each tetrafunctional unit present in the copolymer and (B) a polydiorganosiloxane, wherein the improvement comprises the combination of an amino-functional drug to be delivered from said drug delivery mesas and a biocompatible silicone pressure-sensitive adhesive composition which has been chemically treated to reduce the silicon-bonded hydroxyl content of the composition to a sufficient degree to thereby render said adhesive more resistant to the loss of tack and ability to instantly adhere to the skin caused by contact with said amino-functional drug.

This invention also relates to a method of maintaining the instant adherence to the skin of a wearer of a transdermal drug delivery device for the controlled transdermal delivery of an amino-functional drug wherein said device is maintained in contact with the skin by a skin-contacting silicone pressure-sensitive adhesive layer wherein the method which comprises providing said device with a silicone pressure-sensitive adhesive layer formed of a silicone pressure-sensitive adhesive composition of the type described above and further detailed, infra. "Instant adherence" is intended to mean that the device is sufficiently tacky to the touch to be able to adhere instantly to the skin after application to the skin without an undue mount of pressure being exerted against the device to get it to adhere to the skin.

The "amino-functional" drugs to be delivered for therapeutic purposes can be those which are amenable to being delivered transdermally and can contain one or more primary amine radicals such as phenylpropanolamine, secondary amine radicals such as propranolol, tertiary amine radicals such as theophylline and chlorpheniramine. The term "amino-functional" also includes heterocyclic amine radicals such as those found in theophylline and diethylcarbomazine and salts of amino-functional drugs such as scopolamine hydrobromide provided that they can be delivered transdermally, but does not include oxidized nitrogen radicals such as nitro radicals. Other examples of amino-functional drugs for transdermal drug delivery are ephedrine, fentanyl and atropine. Other examples of amino-functional drugs for use in transdermal drug delivery systems will be apparent to those skilled in the art. See, for example, the Zaffaroni patents cited above and pages 149–217 Yie Chien's treatise entitled "Novel Drug Delivery Systems" which is Volume 14 of Drugs and the Pharmaceutical Sciences, Marcel Dekker, Inc., New York, N.Y. 10016 (1982) for further information on amino-functional drugs and drugs suitable for transdermal delivery.

Without wishing to be bound by a theory of operation, it appears that amine radicals act as catalysts for the condensation of silicon-bonded hydroxyl groups in silicone pressure-sensitive adhesives. See Canadian Pat. No. 575,664 to Bartell (issued May 12, 1959) and British Pat. No. 859,511 to Lamason (published Jan. 25, 1961) for the use of amines as a curing catalyst for silicone pressure-sensitive adhesives. Thus, amino-functional drugs which contain radicals capable of catalyzing that condensation are also capable of causing silicone pressure-sensitive adhesives containing a sufficient level of silicon-bonded hydroxyl radicals to condense and thereby lose their tack and ability to instantly adhere to the skin upon aging. Loss of tack is particularly noticeable when the tack value of the adhesive is desired to be relatively low ($<100 g/cm^2$) to avoid damage to the skin. Such low tack adhesive compositions generally contain about 60 to 70 parts by weight of resinous copolymer and 30 to 40 parts by weight of polydiorganosiloxane based on a total of 100 parts by weight of both ingredients. Generally, one observes greater detrimental effects on tack and other physical properties of the pressure-sensitive adhesive compositions with adhesives having lower tack values ("drier adhesives" where the term "dry" means no tack to a light touch) and higher resin copolymer contents. It was found that more strongly basic amino-functional drugs wherein the most basic amino-functional radical had a basic pKa of about 8.5 or more (pKa is the negative logarithm of the dissociation constant of the amino-functional radical in aqueous solution) were found to have a greater effect on tack than those having a pKa of less than about 8.5, particularly with lower tack adhesives.

Silicone pressure-sensitive adhesive compositions preferred for use in the method and device of the present invention are described in the following U.S. patent applications, which were filed on Oct. 29, 1984, are assigned to the same assignee as is the present invention and are hereby incorporated by reference to teach compositions useful in this invention: "Silicone Pressure-Sensitive Adhesive Process and Product Thereof" to John D. Blizzard and Terence John Swihart, (U.S. Ser. No. 06/665,797, now U.S. Pat. No. 4,591,622); "Silicone Pressure-Sensitive Adhesive Process and Product With Improved Lap-Shear Stability-I" to John D. Blizzard and Dipak Narula (U.S. Ser. No. 06/665,805, now U.S. Pat. No. 4,584,355); and "Silicone Pressure-Sensitive Adhesive Process and Product With Improved Lap-Shear Stability-II" to Gary R. Homan and Harold L. Vincent (U.S. Ser. No. 06/665,796, now U.S. Pat. No. 4,585,836). Any adhesive layers used for this purpose must of course be biocompatible and that can be evaluated by the use of standard testing procedures.

The manner in which preferred silicone pressure-sensitive compositions may be prepared will now be described. Further details and examples of compositions can be found in the aforementioned Blizzard and Swihart, Blizzard and Narula, and Homan, et al. patent applications.

One type of silicone pressure-sensitive adhesive composition employs a composition made by the method of the Blizzard and Swihart Patent Application which comprises the steps of:

(I) mixing (A) from 40 to 70 inclusive parts by weight of at least one benzene soluble resin copolymer containing silicon-bonded hydroxyl radicals and consisting essentially of $R_3SiO_{1/2}$ units and $SiO_{4/2}$ units in a mole ratio of 0.6 to 0.9 $R_3SiO_{1/2}$ units for each $SiO_{4/2}$ unit present, (B) from 30 to 60 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. where each T is R— or X—, (C) a sufficient amount of at least one organosilicon endblocking agent capable of generating an endblocking triorganosilyl unit selected from the group consisting of $ZR_2Si$— units, $CH_3Z'$— units and RZ"— units and $Z'''R_2Si$— units to provide a 1:0.8 to 1:3 mole ratio of total silicon-bonded hydroxyl and X radicals present in said (A) and (B) to total endblocking triorganosilyl units provided by all endblocking agent present, said agent being selected from the group consisting of $ZR_2SiY$, $(ZR_2Si)_qD$, $CH_3Z'Y$, $(CH_3Z')_2O$, RZ"Y', $(RZ'')_2O$ and $Z'''R_2SiY'$, (D) when desirable, an additional catalytic amount of a mild silanol condensation catalyst in the event that none is provided by said (C), and (E) when necessary, an effective mount of an organic solvent which is inert with respect to (A), (B), (C) and (D) to reduce the viscosity of a mixture of (A), (B), (C), and (D), and (II) condensing the mixture of (A), (B), (C) and (D) at least until a substantial amount of the endblocking triorganosilyl units have reacted with the silicon-bonded hydroxyl radicals and X radicals of said (A) and (B), wherein each R is a monovalent organic radical selected from the group consisting of hydrocarbon radicals of from 1 to 6 inclusive carbon atoms, each X radical is selected from the group consisting of HO—, H— and R'O— radicals, each R' is an alkyl radical of from 1 to 4 inclusive carbon atoms, each Y radical is a monovalent hydrolyzable organic radical or HO—, each Y' is HO— or a monovalent hydrolyzable organic radical free of nitrogen, each A radical is selected from the group consisting of R— and halohydrocarbon radicals of from 1 to 6 inclusive carbon atoms, each Z radical is A— or QR"—, each R" is a divalent alkylene radical of from 1 to 6 inclusive carbon atoms, each Q is an organofunctional monovalent radical selected from the group consisting of RCOE'—, RE'OC—, NC—, R'E'—, HO—, $G_2N$—, $HO(R''O)_n$—, and $G_2NCH_2CH_2NG$— where E' is —O—, —NG— or —S—, n has a value of from 1 to 6,

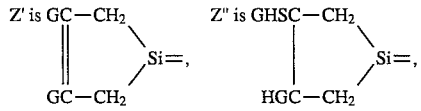

Z''' is selected from the group consisting of HSR"—, $HSCH_2CH_2NGR''$— and $HOCH_2CH_2SR''$— radicals, each G is R'— or H—, D is a divalent or trivalent organic radical capable of being hydrolyzed to release said endblocking silyl units and q has a value of 2 when D is a divalent radical and q has a value of 3 when D is a trivalent radical.

The pressure-sensitive adhesive compositions are made in accordance with the present invention using from 40 to 70 inclusive parts by weight of silicone copolymer resins (A) and from 30 to 60 parts by weight of polydiorganosiloxanes (B) of the type which have been used in the past to make such compositions. More preferred are compositions employing from 50 to 65 parts by weight of resin copolymer (A) and from 35 to 50 parts by weight of polydiorganosiloxane (B). For low tack adhesives, compositions having 58 to 65 parts by weight of resin copolymer (A) and from 35 to 42 parts by weight of polydiorganosiloxanes (B) are preferred.

The benzene-soluble silicone resin copolymers (A) are well-known materials. They contain silicon-bonded hydroxyl radicals in amounts which typically range from about 1 to 4 weight percent of silicon-bonded hydroxyl radicals and consist essentially of triorganosiloxy units of the formula $R_3SiO_{1/2}$ and tetrafunctional siloxy units of the formula $SiO_{4/2}$ in a mole ratio of from 0.6 to 0.9 $R_3Si_{1/2}$ units for each $SiO_{4/2}$ unit present. Blends of two or more such copolymers may also be used. There should be at least some and preferably at least 0.5% silicon-bonded hydroxyl content to enable the polydiorganosiloxane component to copolymerize with the copolymer resin and/or to react with the endblocking agent being added to chemically treat the silicone pressure-sensitive adhesive composition. These resin copolymers are benzene-soluble resinous materials which are typically solids at room temperature and are prepared as, and usually, but not necessarily used as, a solution in an organic solvent. Typical organic solvents used to dissolve resin copolymer (A) include benzene, toluene, xylene, methylene chloride, perchloroethylene, naphtha mineral spirits and mixtures of these.

Resin copolymer (A) consists essentially of from 0.6 to 0.9 $R_3SiO_{1/2}$ units for every $SiO_{4/2}$ unit in the copolymer. There may also be a few mole percent of $R_2SiO$ units present in the copolymer provided that the presence of such units does not cause the ultimate product of this process to lose its ability to function as a pressure-sensitive adhesive. Each R denotes, independently, a monovalent hydrocarbon radical having from 1 to 6 inclusive carbon atoms such as methyl, ethyl, propyl, isopropyl, hexyl, cyclohexyl, vinyl, allyl, propenyl and phenyl. Preferably, the $R_3SiO_{1/2}$ units are $Me_2R'''SiO_{1/2}$ units wherein is R''' is a methyl ("Me"), vinyl ("Vi") or phenyl ("Ph") radical. More preferably, no more than 10 mole percent of the $R_3SiO_{1/2}$ units present in resin copolymer (A) are $Me_2R''''SiO_{1/2}$ units and the remaining units are $Me_3SiO_{1/2}$ units where each R'''' is a methyl or a vinyl radical.

The mole ratio of $R_3SiO_{1/2}$ and $SiO_{4/2}$ units can be determined simply from a knowledge of the identity of the R radicals in the $R_3SiO_{1/2}$ units and the percent carbon analysis of the resin copolymer. In the preferred resin copolymer consisting of from 0.6 to 0.9 $Me_3SiO_{1/2}$ units for every $SiO_{4/2}$ unit, the carbon analysis has a value of from 19.8 to 24.4 percent by weight.

Resin copolymer (A) may be prepared according to Daudt et al., U.S. Pat. No. 2,676,182 (issued 4/20/54 and hereby incorporated by reference) whereby a silica hydrosol is treated at a low pH with a source of $R_3SiO_{1/2}$ units such as a hexaorganodisiloxane such as $Me_3SiOSiMe_3$, $ViMe_2SiOSiMe_2Vi$ or MeViPhSiOSiPhViMe or triorganosilane such as $Me_3SiCl$, $Me_2ViSiCl$ or MeViPhSiCl. Such copolymer resins are typically made such that the copolymer resin contains about 1 to 4 weight percent of silicon-bonded hydroxyl radicals. Alternatively, a mixture of suitable hydrolyzable silanes free of R radicals may be cohydrolyzed and condensed. In this alternative procedure, it is a typical practice to further treat the copolymer product with a suitable silylating agent, such as hexamethyldisilazane or divinyltetramethyldisilazane, to reduce the silicon-bonded hydroxyl content of the copolymer product to less that 1 percent by weight. This step would not be necessary, but could be used, in the Blizzard and Swihart process now being described. Preferably, the resin copolymers employed contain from about 1 to 4 weight percent of silicon-bonded hydroxyl radicals.

Ingredient (B) is also a well-known material and is one or more polydiorganosiloxanes consisting essentially of ARSiO units terminated with endblocking $TRASiO_{1/2}$ units, each of which polydiorganosiloxanes has a viscosity of from 100 centipoise to 30,000,000 centipoise at 25° C. (100 millipascal-seconds to 30,000 pascal seconds (Pa.s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25° C. range from fluids to somewhat viscous polymers. These polydiorganosiloxanes are preferably prereacted with resin copolymer (A) prior to condensation in the presence of endblocking agent (C) to improve the tack and adhesion properties of the resulting pressure-sensitive adhesive as will be further described. Polydiorganosiloxanes having viscosities in excess of 100,000 centipoise can typically be subjected to the condensation/endblocking step (II) of the present invention without prereaction. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity Value of about 50 mils (1.27 mm) or more at 25° C.).

The polydiorganosiloxanes of (B) consist essentially of ARSiO units where each R is as defined above. Each A radical is selected from radicals such as R— or halohydrocarbon radicals of from 1 to 6 inclusive carbon atoms such a chloromethyl, chloropropyl, 1-chloro,-2-methylpropyl, 3,3,3,-trifluoropropyl and $F_3C(CH_2)_5$— radicals. Thus the polydiorganosiloxane can contain $Me_2SiO$ units, PhMeSiO units, MeViSiO units, $Ph_2SiO$ units, methylethylsiloxy units 3,3,3-trifluoropropyl units and 1-chloro, 2-methylpropyl units and the like. Preferably, the ARSiO units are selected from the group consisting of R'''2SiO units, $Ph_2SiO$ units and combinations of both where R''' is as above, at least 50 mole percent of the R''' radicals present in the polydiorganosiloxane (B) are methyl radicals and no more than 50 mole percent of the total moles of ARSiO units present in each polydiorganosiloxane of (B) are $Ph_2SiO$ units. More preferably, no more than 10 mole percent of the ARSiO units present in each polydiorganosiloxane (B) are MeR''''SiO units where R'''' is as above defined and the remaining ARSiO units present in each polydiorganosiloxane are $Me_2SiO$ units.

Each polydiorganosiloxane (B) is terminated with endblocking units of the unit formula $TRASiO_{1/2}$ where R and A are as defined above and each T radical is R or X wherein each X radical is selected from the group consisting of HO—, H— and R'O— radicals where each R' is an alkyl radical of from 1 to 4 inclusive carbon atoms such as methyl, ethyl, n-propyl, and isobutyl radicals. The X radicals provide a site for reaction with the endblocking triorganosilyl units of ingredient (C) and also provide a site for condensation with other X radicals on polydiorganosiloxanes (B) or with the silicon-bonded hydroxyl groups present in resin copolymer (A). Use of polydiorganosiloxanes where T is HO— is most preferred because the polydiorganosiloxane (B) can then readily copolymerize with the resin copolymer (A). When an appropriate catalyst such as HCl which is generated when chlorosilanes are used or ammonia which is generated when organosilazanes are used as endblocking agents, triorganosiloxy (e.g., $R_3SiO_{1/2}$ such as $(CH_3)_3SiO_{1/2}$ or $CH_2{=}CH(CH_3)_2SiO_{1/2}$) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing X radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by the following U.S. Pat. Nos.: 2,490,357 (Hyde); 2,542,334 (Hyde); 2,927,907 (Polmanteer); 3,002,951 (Johannson); 3,161,614 (Brown, et al.); 3,186,967 (Nitzche, et al.); 3,509,191 ((Atweil) and 3,697,473 (Polmanteer, et al.) which are hereby incorporated by reference.

To obtain pressure-sensitive adhesives which are to be cured by peroxide or through aliphatically unsaturated radicals present in resin copolymer (A) or polydiorganosiloxane (B), if resin copolymer (A) contains aliphatically unsaturated radicals, then polydiorganosiloxane (B) should be free of such radicals and vice-versa. If both components contain aliphatically unsaturated radicals, curing through such radicals can result in products which do not act as pressure-sensitive adhesives.

The distinguishing feature of the present invention is the use of a silicone pressure-sensitive adhesive composition which has been chemically treated to reduce its silicon-bonded hydroxyl content to render it more suitable for use with amino-functional transdermal drug delivery devices. The chemical treatment is preferably accomplished by conducting the condensation of resin copolymer (A) and polydiorganosiloxane (B) in the presence of at least one organosilicon endblocking agent (C) capable of generating endblocking triorganosilyl units of the formula $ZR_2Si$—, $CH_3Z'$— units where Z' is

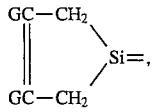

RZ"— where Z" is

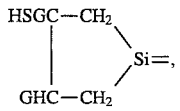

and $Z'''R_2Si$— units where Z''' is HSR"— such as $HSCH_2CH_2CH_2$—, $HSCH_2CH_2NGR''$— such as $HSCH_2CH_2NH(CH_2)_3$— or $HOCH_2CH_2SR''$— such as $HOCH_2CH_2SCH_2CH_2CH_2$—. The Z' radicals are silacyclopentenyl radicals and are described in Atwell U.S. Pat. No. 3,509,191 (issued 4/28/70) and the Z" radicals are described in U.S. Pat. No. 3,655,713. The endblocking agent capable of providing such triorganosilyl units is selected from the group consisting of $ZR_2SiY$, $(ZR_2Si)_qD$, $CH_3Z'Y$, $(CH_3Z')_2O$, RZ"Y', $(RZ'')_2O$ and $Z'''R_2SiY'$ where R is as previously defined and each G is R'— or H—. Preferably, the endblocking agent is selected from the group consisting of $AR_2SiY$, $(AR_2Si)_2D$ and mixtures thereof and each R present in the endblocking agent is a methyl or a phenyl radical. It is preferred to use endblocking agents having the same Y or D radicals if mixtures are to be used.

Each Y radical is HO— or a monovalent hydrolyzable organic radical such as R'O—, halogen such as Cl— or Br—, amino such as $G_2N$— such as —$NR''''_2$, carboxyl such as $GCH_2COO$— such as acetoxy, $GCH_2CONH$— such as $CH_3CONH$—, urea derivatives such as $(C_2H_5)_2NCO(C_4H_9)$— and the like or H— where R' is as previously defined. Preferably, each Y is R'O—, Cl—, HO—, or $G_2N$— and more preferably, Y is R'O— or Cl—. Y' is HO— or a monovalent hydrolyzable organic radical free of nitrogen such as R'O—. D is selected from the group consisting of divalent and trivalent hydrolyzable radicals such as —O—, —NG—, —NHCONH—, and =N— and q has a value of 2 when D is a divalent radical and q has a value of 3 when D is a trivalent radical. Preferably, q is 2 and D is —NH—.

Each Z radical is selected from radicals such as A— and QR"— radicals where A is as previously defined and R" is a divalent alkylene radical of from 1 to 6 inclusive carbon atoms such as ethylene, propylene, 2-methylpropylene and butylene.

Each Q is a monovalent organofunctional radical which is useful in altering the physical properties of the pressure-sensitive adhesive film. Endblocking agents containing Z''' radicals can be used similarly. Preferably, the Q and Z''' radicals do not condense with the silanol radicals present in the resin copolymer (A) and/or with the X radicals present in polydiorganosiloxane (B) during the condensation step (II) of the present invention. Q can be a monovalent radical selected from the group consisting of RCOE'— where E' is —O—, —NH— or —S— such as RCOO— such as $CH_3COO$—, $CH_2{=}CCH_3COO$—, and $CH_3(CH_2)_3COO$—, RCONH— such as $CH_3CONH$—, and RCOS— such as $CH_3CH_2COS$—, RE'OC— such as $C_2H_5OOC$—, $CH_3CH_2CH_2CH_2NHOC$— and $CH_3CH_2CH_2SOC$—, cyano which is NC—, HO—, R'E'— such as $CH_3CH_2CH_2O$—, and R'S— such as $CH_3CH_2CH_2S$—, and $G_2N$— such as $H_2N$— and $C_2H_5NH$—, $HO(R''O)_n$— where n has a value of from 1 to 6 such as $HOCH_2CH_2O$—, $G_2NCHCH_2NG$— such as $H_2NCH_2CH_2NH$—.

Preferably, Z is selected from the group consisting of methyl, vinyl and 3,3,3-trifluoropropyl radicals and more preferably is a methyl or vinyl radical.

Endblocking agents capable of providing endblocking triorganosilyl units are commonly employed as silylating agents and a wide variety of such agents are known. A single endblocking agent such as hexamethyldisilazane can be employed or a mixture of such agents such as hexamethyldisilazane and sym-tetramethyldivinyldisilazane can be employed to vary the physical properties of the pressure-sensitive adhesive film. For example, use of an endblocking agent containing fluorinated triorganosilyl units such as $[(CF_3CH_2CH_2)Me_2Si]_2NH$ in the process of the present invention could result in a silicone pressure-sensitive adhesive having improved resistance to hydrocarbon solvents after the film is deposited and the presence of the fluorinated triorganosilyl units could affect the tack and adhesion properties of the pressure-sensitive adhesive when the R radicals present in the resin copolymer (A) and the polydiorganosiloxane (B) are substantially composed of methyl radicals. By employing endblocking agents containing higher carbon content silicon-bonded organic radicals such as ethyl, propyl or hexyl radicals, the compatibility of the silicone pressure-sensitive adhesive with organic pressure-sensitive adhesives could be improved to allow blending of such adhesives to obtain improved adhesive compositions. Use of endblocking agents having triorganosilyl units having organofunctional radicals such as amides, esters, ethers and cyano radicals could allow one to change the release properties of a pressure-sensitive adhesive made in accordance with the present invention. Likewise, organofunctional radicals present in the pressure-sensitive adhesive composition can be altered such as by hydrolyzing ROOCR" radicals to generate HOOCR"— radicals which are converted to MOOCR" radicals where M is a metal cation such as lithium, potassium or sodium. The resulting composition may then exhibit release or other properties different from a composition containing RCOOR"— radicals.

Use of endblocking agents containing triorganosilyl units with unsaturated organic radicals such as vinyl can produce silicone pressure-sensitive adhesives which can be cross-linked through such groups. For example, an organosilicon cross-linking compound containing silicon-bonded hydrogen radicals can be added along with a noble metal such as a platinum metal or rhodium metal catalyst to a silicone pressure-sensitive adhesive composition made in accordance with the present invention which contains PhMeViSi— and $Me_3Si$— endblocking triorganosilyl units to produce a pressure-sensitive adhesive composition which cures via the noble metal catalyzed addition of silicon-bonded hydrogen radicals to silicon-bonded vinyl radicals. Use of endblocking agents containing triorganosilyl units with phenyl radicals could improve the stability of the pressure-sensitive adhesive to heat.

Thus, the endblocking agent serves several purposes in the present invention because it removes silicon-bonded hydroxyl radicals which can affect the stability of the resulting pressure sensitive adhesive layer with respect to amino-functional drugs, it enables one to modify the properties of the adhesive without making substantial changes in the resin copolymer and polydiorganosiloxanes and by selecting an appropriate level of endblocking agent, one can alter the molecular weight and thereby the properties of the condensation product of the resin copolymer (A) and polydiorganosiloxane (B) since the triorganosilyl units act as endblocking units.

In order to achieve the above, one must add at least a sufficient amount of one or more endblocking agents to provide at least a 0.8:1 mole ratio of total endblocking triorganosilyl units to total silicon-bonded hydroxyl radicals present in resin copolymer (A) and polydiorganosiloxane (B). A 1:1 ratio may not always be necessary since condensation between the resin copolymer (A) and polydiorganosiloxane (B) also effectively removes silicon-bonded hydroxyl radicals. The resin copolymer (A) will typically contain the majority of the silicon-bonded hydroxyl content present in the combination of resin copolymer (A) and polydiorganosiloxane (B). A number of methods for determining silicon-bonded hydroxyl content exist, but results with polymers of the resin copolymer (A) type tend to be variable. Therefore it is better to include a sufficient excess of endblocking agent to provide at least an 10% excess (0.88:1 mole ratio of endblocking triorganosilyl units to the silicon-bonded hydroxyl radicals). When the purpose is only to remove a substantial amount of the residual silicon-bonded hydroxyl content e.g., using a heating step to effect condensation of resin copolymer (A) with polydiorganosiloxane (B) in addition to endblocking, the minimum plus the aforementioned excess of endblocking agent is preferred. To obtain maximum resistance to amino-functional drugs, it is best to use a substantial excess of endblocking agent to silicon-bonded hydroxyl radical content. A 2:1 mole ratio of endblocking triorganosilyl units to silicon-bonded hydroxyl radicals present has produced adhesives which are quite resistant to loss of tack, particularly when the silanol condensation catalysts described, infra, are also employed. Increasing the extent of endblocking of silicon-bonded hydroxyl radicals such as by using larger levels of endblocking agent appear to reduce the sensitivity of the resulting pressure-sensitive adhesive to the effect of amino-functional compounds.

When one desires to alter the properties of the pressure-sensitive adhesive by including endblocking agents with specific radicals, it is desirable to use a resin copolymer (A) that has a higher silicon-bonded hydroxyl content (e.g., 1–4 weight percent) so that more of the triorganosilyl units confining such radicals will be reacted into the condensation product of resin copolymer (A) and polydiorganosiloxane (B). Since a condensation process can also occur in the process of the present invention, inclusion of greater than the stoichiometric amount of endblocking triorganosilyl units relative to the silicon-bonded hydroxyl radical and X radicals can affect the molecular weight of the condensation product which is the silicone pressure-sensitive adhesive. Use of more than a 1:3 mole ratio of total silicon-bonded hydroxyl radicals and X radicals present in resin copolymer (A) polydiorganosiloxane (B) to total endblocking triorganosilyl units provided by the endblocking agents added is believed to be excessive and wasteful.

Examples of endblocking agents are $(Me_3Si)_2NH$, $(ViMe_2Si)_2NH$, $(MePhViSi)_2NH$, $(CF_3CH_2CH_2Me_2Si)_2NH$, $(Me_3Si)_2NMe$, $(ClCH_2Me_2Si)_2NH$, $Me_3SiOMe$, $Me_3SiOC_2H_5$, $Ph_3SiOC_2H_5$, $(C_2H_5)_3SiOC_2H_5$, $Me_2PhSiOC_2H_5$, $(i\text{-}C_3H_7)_3SiOH$, $Me_3Si(OC_3H_7)$,

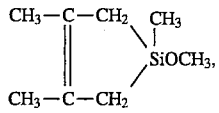

$MePhViSiOMe$, $Me_3SiCl$, $Me_2ViSiCl$, $MePhViSiCl$, $(H_2C{=}CHCH_2)Me_2SiCl$, $(n\text{-}C_3H_7)_3SiCl$, $(F_3CCF_2CF_2CH_2CH_2)_3SiCl$, $NCCH_2CH_2Me_2SiCl$, $(n\text{-}C_6H_{13})_3SiCl$, $MePh_2SiCl$, $Me_3SiBr$, $(t\text{-}C_4H_9)Me_2SiCl$, $CF_3CH_2CH_2Me_2SiCl$, $(Me_3Si)_2O$, $(Me_2PhSi)_2O$, $BrCH_2Me_2SiOSiMe_3$, $(p\text{-}FC_6H_4Me_2Si)_2O$, $(CH_3COOCH_2Me_2Si)_2O$, $[(H_2C{=}CCH_3COOCH_2CH_2)Me_2Si]_2O$, $[(CH_3COOCH_2CH_2CH_2)Me_2Si]_2O$, $[(C_2H_5OOCCH_2CH_2)Me_2Si]_2O$, $[(H_2C{=}CHCOOCH_2)Me_2Si]_2O$,

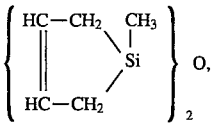

$(Me_3Si)_2S$, $(Me_3Si)_3N$, $Me_3SiNHCONHSiMe_3$, $F_3CH_2CH_2Me_2SiNMeCOCH_3$, $(Me_3Si)(C_4H_9)NCON(C_2H_5)_2$, $(Me_3Si)PhNCONHPh$, $Me_3SiNHMe$, $Me_3SiN(C_2H_5)_2$, $Ph_3SiNH_2$, $Me_3SiNHOCCH_3$, $Me_3SiOOCCH_3$, $[(CH_3CONHCH_2CH_2CH_2)Me_2Si]_2O$, $Me_3SiO(CH_2)_4OSiMe_3$, $Me_3SiNHOCCH_3$, $Me_3SiC{=}CH$

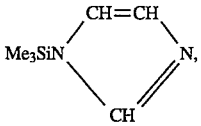

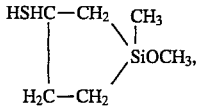

$[HO(CH_2)_4Me_2Si]_2O$, $(HOCH_2CH_2OCH_2Me_2Si)_2O$, $H_2N(CH_2)_3Me_2SiOCH_3$, $CH_3CH(CH_2NH_2)CH_2Me_2SiOCH_3$, $C_2H_5NHCH_2CH_2S(CH_2)_6Me_2SiOC_2H_5$, $HSCH_2CH_2NH(CH_2)_4Me_2SiOC_2H_5$, $HOCH_2CH_2SCH_2Me_2SiOCH_3$.

Preferably, the endblocking agents employed are of the type $(AR_2Si)_2NH$ such as $(Me_3Si)_2NH$, $AR_2SiOR'$ or $AR_2SiCl$.

A number of the above endblocking agents generate silanol condensation catalysts such as acids such as hydrogen chloride and bases such as ammonia or amines when the triorganosilyl unit reacts with silicon-bonded hydroxyl radicals and/or X radicals present in the resin copolymer (A) and polydiorganosiloxanes (B). As will be further described, the condensation step (II) of the present invention is preferably done with heating and the presence of the catalyst causes the condensation of the resin copolymer (A) and polydiorganosiloxanes (B) to take place at the same time that endblocking by the endblocking triorganosilyl units occurs. Depending on the method of manufacture employed, resin copolymer (A) and/or polydiorganosiloxane (B) may contain a sufficient level of residual catalyst to effect condensation and endblocking. Thus, if desired, an additional catalytic amount of a "mild" silanol condensation catalyst can be used where the term "mild" means that it causes the endblocking agent to condense with the resin copolymer (A) and the polydiorganosiloxane (B) while causing minimal siloxane bond rearrangement. Examples of "mild" catalysts are those known to be used as curing agents for pressure-sensitive adhesive compositions such as amines such as triethylamine and organic compounds such as tetramethylguanidine 2-ethylcaproate, tetramethylguanidine 2-ethylhexanoate and n-hexylamine 2-ethylcaproate. The additional catalyst (D) selected should not cause an excessive amount of cleavage of siloxane bonds in the resin copolymer (A) and/or polydiorganosiloxane (B) during the condensation reaction thereby resulting in gelation of the composition or a substantial loss of adhesive properties as is known to happen with organic tin catalysts and strong acids. Preferably, catalyst (D) is only used when no catalyst is provided by endblocking agent (C). Suitable catalysts and the selection of specific catalyst and amounts thereof for catalyzing the reaction of particular endblocking triorganosilyl units with the silicon-bonded hydroxyl radicals found on the organosiloxy units present in resin copolymer (A) and polydiorganosiloxane (B) is known to those skilled in the art. Use of a catalyst such as HCl generated by a chlorosilane endblocking agent is preferable when $R_3SiO/_{1/2}$ endblocking units are present in polydiorganosiloxane (B) as noted earlier. Silazane endblocking agents can also be used when T is R— and are preferred when T in the polydiorganosiloxane (B) is H. Preferably, particularly when T in the polydiorganosiloxane (B) is HO—, an endblocking agent of the silazane type is used such that no extra catalyst needs to be added; the ammonia compound generated is generally volatile and can be eliminated more readily than a nonvolatile, solid catalyst material. When the resin copolymer (A) is prepared under acidic conditions as described in the Daudt, et al. patent above, there is often a sufficient level of acid catalyst present to enable endblocking units containing Y radicals of the alkoxy or —OH type to be used without any further addition of a condensation catalyst. Adhesives which are very resistant to the effect of amino-functional drugs have been prepared using trifluoroacetic acid as a catalyst along with a 2:1 molar excess of endblocking agent to silicon-bonded hydroxyl content where the catalyst was added at a level of 0.1 percent by weight of catalyst based on the total weight of the nonvolatile content of resin copolymer (A) and polydiorganosiloxane (B) present as will be shown in the Examples.

When necessary, an effective amount of an organic solvent can be added separately to the mixture of resin copolymer (A) (as a solid material or in organic solvent solution), polydiorganosiloxane (B), endblocking agent (C) and catalyst (D) to reduce the viscosity thereof or else can be present as a result of the fact that (A) and/or (B) was added as a solvent solution. The organic solvent should be inert towards the other components of the mixture and not react with them during the condensation step. As noted earlier, resin copolymer (A) is often made as a solvent solution in toluene or xylene. Use of an organic solvent is often necessary when polydiorganosiloxane (B) is in the form of a high viscosity gum which results in a high viscosity mixture even when the mixture is heated to typical processing temperatures of 100°–150° C. Use of an organic solvent which permits azeotropic removal of water is preferred. The term "organic solvent" includes a single solvent such as benzene, toluene, xylene, trichloroethylene, perchloroethylene, ketones, halogenated hydrocarbons such as dichlorodifluoromethane, naphtha mineral spirits and mixtures of two or more organic solvents to form a blended organic solvent. Use of a ketone such as methylisobutyl ketone as at least a portion of the solvent is preferred when fluorinated radicals are present on a major amount of the siloxane or silyl units present in polydiorganosiloxane (B) for compatibility reasons. Preferably, the mixture contains a hydrocarbon solvent selected from the group consisting of benzene, toluene and xylene.

In accordance with step (I) of the present invention, resin copolymer (A), polydiorganosiloxane (B), are mixed together with any organic solvent (E) that is to be added. While the condensation reaction may take place at room temperature if a suitably reactive silylating agent such as a silazane such as hexamethyldisilazane or a suitable catalyst such as tetramethylguanidine 2-ethylhexanoate is added and, optionally, with vacuum stripping of condensation by-products,the preferred method is to conduct the condensation reaction with heating and more preferably, at 80°–100° C. Thus, the preferred method involves mixing (A), (B) and (E) until the mixture is uniform followed by the addition of endblocking agent (C) and, last, any condensation catalyst (D) for the endblocking reaction to be added.

The condensation step (II) is begun when addition of a suitably reactive endblocking agent such as a silazane or a catalyst is made if the reaction is to take place at room temperature or else begins when the mixture is heated from 80° C. to 160° C., preferably at 80°–100° C. Condensation is preferably allowed to proceed at least until the rate of evolution of condensation byproducts such as water is substantially constant. Heating is then continued until the desired physical properties such as viscosity, tack and adhesion values are obtained. Typically the mixture is allowed to reflux for an additional 1 to 4 hours after the rate of evolution of condensation by-products is substantially constant. Longer condensation times may be needed for compositions containing organofunctional groups such as fluorinated radicals on the polydiorganosiloxane (B) and/or endblocking agent which are less compatible with those present on the copolymer (A). When the condensation reaction is complete, the residual endblocking agent is solvent stripped away by removing excess solvent during or after the azeotropic removal of condensation by-products. The nonvolatile solids content of the resulting silicone pressure-sensitive adhesive composition can be adjusted by adding or removing solvent, the solvent present can be completely removed and a different organic solvent added to the silicone pressure-sensitive adhesive product, the solvent can be removed completely if the condensation product is sufficiently low in viscosity or else the mixture can be recovered and used as is. Presently, it is preferred to have the pressure-sensitive adhesive compositions in organic solvent solution wherein the organic solvent comprises from 30 to 70 weight percent of the total mixture of (A), (B), (C), (D), and (E), particularly when the polydiorganosiloxane of (B) has a viscosity at 25° C. of greater than 100,000 centipoise.

The above procedure is preferred for compositions wherein the polydiorganosiloxanes (B) are greater than about 100,000 centipoise in viscosity at 25° C. When the viscosity of the polydiorganosiloxanes (B) are less than about 100,000 centipoise at 25° C., the physical properties of pressure-sensitive adhesives obtained therefrom are not always as high in tack and adhesion as may be desired and may also tend to result in adhesives possessing some adhesive transfer between substrates, see for example, the Pail Patent cited above.

For this reason, it is preferred that a precondensation step such as that employed in the Pail Patent be used in the process of the present invention prior to the condensation step in the presence of an endblocking agent (C) be used when a substantial amount of the polydiorganosiloxanes (B)

have a viscosity of less than 100,000 centipoise at 25° C. In this case, Step (I) of the method of the present invention comprises the steps of (Ia) mixing resin copolymers (A), polydiorganosiloxanes (B) and any organic solvent (E) together in the presence of a silanol condensation catalyst of the type previously described (anhydrous ammonia gas is presently preferred), (Ib) condensing (A) and (B) to form a condensed product such as by heating under reflux conditions for 1 to 10 hours and (Ic) mixing the product of step (Ib) with (C), (D) and any further amount of organic solvent (E) which is necessary prior to proceeding with step (II) of the method of the present invention. The product of step (Ib) is thus increased in molecular weight by the precondensation step, but still contains residual silicon-bonded hydroxyl groups which are endblocked in accordance with the present method of the invention to result in an improved pressure sensitive adhesive composition. The resulting silicone pressure-sensitive adhesive composition is then processed according to Step (II) and the solvent can be adjusted as described above to obtain a finished silicone pressure-sensitive adhesive composition.

When endblocking agents which generate ammonia upon reaction with silicon-bonded hydroxyl radicals such as those of the formula $ZR_2SiNH_2$ and the more preferred $(ZR_2Si)_2NH$ are employed, it is preferred that residual ammonia generated by the endblocking agent be removed since the adhesive composition is to be used in a medical application. This can be accomplished in the manner described in the Blizzard and Narula Patent Application by modifying the above-described method to employ the above ammonia generating endblocking agents, preferably where Z is an A radical, eliminating the use of optional condensation catalyst (D) during the step involving condensation in the presence of the endblocking agent because the ammonia released functions as such a catalyst and further incorporating water as an ingredient as follows. To obtain the most highly amino-functional drug resistant adhesives, the use of a catalyst such as trifluoroacetic acid is still desirable, or if one does not desire to use a catalyst, and desires to eliminate an ingredient, one can simply increase the ratio of endblocking agent to silicon-bonded hydroxyl radicals in either the Blizzard and Narula method or the Homan, et al. method, infra. Alternatively both a catalyst and an increased amount of endblocking agent is used.

The manner of making compositions via the Blizzard and Narula Patent Application method includes the incorporation of about 0.5 to 10 moles of water per mole of =NH provided by all endblocking agent (C) present in the composition. 0.5 moles of water would be an effective minimum with the use of at least 1.0 moles of water being more preferred and higher levels such as at least 3 moles of water per mole of =NH being preferred to obtain optimum removal of ammonia from the composition, particularly where the silicon-bonded hydroxyl content is from resin copolymer (A). Use of more than about 10 moles of water per mole of =NH appears to be wasteful.

In the most preferred manner of making silicone pressure-sensitive adhesive compositions wherein the aforementioned ammonia generating endblocking agents are employed, the method taught in the Homan, et al. Patent Application is employed. However, if the adhesive composition is stripped of volatile solvents during processing, such as to substitute one solvent for another as is described in the Examples, use of alcohol as described by Homan, et al. may not be needed. Use of the Blizzard and Narula method which employs water to assist in the removal of residual ammonia from the adhesive compositions is effective for most purposes in practicing the present invention. This method is similar to that described above for the Blizzard and Narula Patent Application method and includes the incorporation of 0.1 to 10 moles of water per mole of =NH provided by all endblocking agent (C) present in the composition. The amount of water added does not appear to be critical; 0.1 moles of water appears to be an effective minimum while more than about 10 moles of water per mole of =NH appears to be wasteful.

The Homan, et al. Patent Application further includes the use of from 0.001 to 10 parts by weight per 100 parts by weight of resin copolymer (A) and polydiorganosiloxane (B) of at least one "ammonia scavenger compound". An "ammonia scavenger compound" is an organofunctional compound such as an alcohol which has one or more polar sites such as a hydroxyl radical and one or more non-polar sites. While not wishing to be limited to a particular theory of operation, the polar portion of the ammonia scavenger compound functions to associate with the ammonia generated by the endblocking agent more strongly than with the silicone portion of the composition to enable it to be removed from the composition when it is no longer needed. The ammonia scavenger compound must have a sufficiently non-polar character to enable that portion of the compound to associate with the non-polar portions of the silicone pressure-sensitive adhesive composition to enable it to make its polar site available for association with the ammonia being released from the endblocking agent. The ammonia scavenger compound must also be sufficiently volatile to be capable of being stripped from the pressure-sensitive adhesive composition at the temperatures at which the composition is being processed (typically 80° C. to 160° C.). The ammonia scavenger compound appears to work synergistically with the added water to greatly increase lap shear stability, particularly the resistance to creep measured in accordance with the stringent procedure set out in U.S. MIL-T-81287, of silicone pressure-sensitive adhesives of the Blizzard and Swihart type and therefore appears to be efficient at removing ammonia which is one factor that can reduce lap shear stability. Very small amounts of ammonia scavenger compounds such as about 0.001 parts per 100 parts of total resin copolymer (A) and polydiorganosiloxane (B) appear to greatly increase the lap shear stability while the use of more than about 10 parts of the compound is believed to be wasteful. Since the silicone pressure-sensitive adhesives are to be used in a medical device, it is best to use adhesives which are as free as possible of non-critical by-products such as ammonia or reactants and catalysts used to manufacture such adhesives.

Examples of ammonia scavenger compounds are those such as alcohols of the formula $HOC_mH_{2m+1}$ where m has a value of from 2 to 4 such as ethanol, iso-propanol, n-butanol and isobutanol; glycol ethers of the formula $HOC_xH_{2x}(OC_xH_{2x})_y(O)_vH$ where x has a value of from 2 to 6, y has a value of from 0 to 3 and v has a value of 0 or 1 such as ethylene glycol, propylene glycol, hexylene glycol, $HOCH_2CH_2OCH_2CH_3$, $HO(CH_2)_6O(CH_2)_6OH$, and $HO(CHCH_3CH_2O)_3H$; ethers of the formula having the formula $C_wH_{2w+1}(OC_xH_{2x})_yOC_wH_{2w+1}$ where w has a value of from 1 to 3 and x and y are as above such as $C_2H_5OC_2H_5$, $C_2H_5OCH_2CH_2OC_2H_5$, $C_2H_5O(CHCH_3CH_2)OC_2H_5$, $C_4H_9O(CHCH_3CH_2)OC_4H_9$, $C_2H_5O(CH_2CH_2O)_3C_2H_5$, and $C_2H_5O(CH_2CH_2O)_2C_2H_5$; esters of the formula $C_wH_{2w+1}C(O)OC_nH_{2n+1}$ and $HC(O)OC_nH_{2n+1}$ where w and n are as defined above such as methyl acetate, ethyl acetate, propyl acetate, amyl acetate, hexylacetate, ethyl formate and ethyl propionate. Most preferred as an ammonia scavenger compound are alcohols. Primary alcohols may be more effective than secondary alcohols followed by tertiary alcohols. Isopropanol, a secondary alcohol, was found to be effective. Just as water alone improves lap shear stability preferably by removing ammonia, the ammonia scavenger compounds alone are expected to improve lap shear stability by removing ammonia.

In accordance with the above preferred Blizzard and Narula or Homan, et al. methods in Step (I) the resin copolymer (A) and polydiorganosiloxane (B), are mixed together with water alone or with water and the ammonia scavenger compound and any organic solvent that is to be added. To accomplish effective removal of the ammonia generated by endblocking agent (C), the preferred method involves conducting the condensation reaction of (A), (B) and (C) with heating at 80° C. to 160° C. and, more preferably, at 80° to 100° C. Thus, after (A), (B), the water or the water and ammonia scavenger, the condensation catalyst (D) and the organic solvent are mixed together, the ammonia generating endblocking agent (C) is added to the mixture. If one is used, a condensation catalyst (D) for the endblocking reaction such as trifluoroacetic acid is added after the endblocking agent (C). The mixture is stirred at room temperature to insure that all ingredients are mixed well. To simplify the procedure, the water or the water and ammonia scavenger compound can be added at the beginning of the procedure although these ingredients could be added at any point during or after the hereinafter-described condensation step (II) since the function of these ingredients is to remove the ammonia from the pressure-sensitive adhesive composition being made. For example, the water or water and ammonia scavenger compound may also be added just prior to the hereinafter-described additional stripping step (III). This may require cooling of the mixture before the lower boiling water and in some cases, the ammonia scavenger compound (when used), can be added. If a condensation catalyst (D) for the endblocking reaction is to be used, it should be added after the addition of endblocking agent (C), but before the hereinafter described condensation step (II).

The condensation step (II) is begun when addition of an ammonia generating endblocking agent (C) is made at room temperature. Condensation continues when the mixture is heated from 80° C. to 160° C., preferably to 80°–100° C. Condensation is preferably allowed to proceed at least until the rate of evolution of condensation by-products such as water is substantially constant. Heating is then continued until the desired physical properties such as viscosity, tack and adhesion values are obtained. Typically the mixture is allowed to reflux for an additional 1 to 4 hours after the rate of evolution of condensation by-products is substantially constant. Longer condensation times may be needed for compositions containing organofunctional radicals such as fluorinated radicals on the polydiorganosiloxane (B) or endblocking agent which are less compatible with those on the resin copolymer (A). During the condensation step and the additional reflux step, condensation by-products are at least periodically removed from the mixture such as by azeotropic removal of by-products or by removing some solvent periodically from the mixture.

Presently, the preferred procedure used when ammonia scavenger compounds are employed (to obtain optimal removal of ammonia from the adhesive composition) is to add the water, the endblocking agent and any condensation catalyst (D) together with (A) and (B) and to conduct the condensation step (II) described above. When that Step (II) is complete, the ammonia scavenger compound is added and the reaction product is held at reflux temperature for a period of time (3 hours is presently preferred although 1–5 hours can also be adequate) to improve removal of ammonia during stripping before the stripping Step (III) is started. This procedure appears to optimize removal of ammonia from the reaction mixture.

When the condensation reaction of the Blizzard and Narula or Homan, et al. method is substantially complete, Step (III) is begun wherein the residual endblocking agent, water or water and ammonia scavenger compound, and any remaining ammonia is solvent stripped away by removing excess solvent during or after the step (II) involving azeotropic removal of condensation by-products. Removal of solvent will carry away more volatile ingredients as part of the solvent or as separate ingredients which are carried with the solvent during stripping. The nonvolatile solids content of the resulting silicone pressure-sensitive adhesive composition can be modified as described, supra. Likewise, a precondensation step of the type described, supra, can be employed prior to carrying out condensation in the presence of the above-described ammonia-generating endblocking agents. Since it is desirable to remove as much volatile material as possible for adhesives to be used in medical products, the Blizzard and Narula, and the Homan, et al. processes are presently preferred as described above.

In a less preferred, but possibly useful alternative silicone pressure-sensitive adhesive composition, the resin copolymer (A) described previously can be condensed with the aforementioned endblocking agents to minimize the level of silicon-bonded hydroxyl content therein. This chemically treated resin copolymer can then simply be cold-blended or further heated with a high molecular weight polydiorganosiloxane gum of the type described as polydiorganosiloxane (B) to obtain a pressure-sensitive adhesive composition wherein the silicon-bonded hydroxyl radical content is minimal because the primary source of silicon-bonded hydroxyl content is from the resin copolymer (A) which has been chemically treated and the silicon-bonded hydroxyl radical content of the high molecular weight polydiorganosiloxane is very low since such radicals will only be found at the terminal siloxy units.

The silicone pressure-sensitive adhesive compositions described above can be used as prepared to prepare pressure-sensitive adhesive films for use on transdermal drug delivery devices in accordance with well-known techniques or else can, optionally, be further cured to increase the cross-link density of the adhesive film to improve the physical properties of the film. Uncured adhesives generally do not have cohesive strengths which are as high as those exhibited by cured adhesives. In accordance with well-known procedures, about 0.5–3% by weight of a peroxide catalyst such as benzoyl peroxide or 2,4-dichlorobenzoyl peroxide based on adhesive solids can be added to the composition and the film can be cured at 110° C. to 200° C. for 1 to 10 minutes. Other free radical cross-linking methods such as electron beam or actinic radiation may be useful in curing adhesive films, particularly when the silicone pressure-sensitive adhesive contains aliphatically unsaturated radicals such as vinyl radicals. When the resin copolymer (A) and/or the endblocking triorganosilyl units of (C) of the silicone pressure-sensitive adhesive contain aliphatically unsaturated radicals such as vinyl radicals, the adhesive can be cured at room temperature or by heating by using an ≡SiH bearing coreactant in conjunction with a chloroplatinic acid catalyst in the well-known manner.

Other well-known ingredients such as fillers or pigments may be added to the silicone pressure-sensitive adhesive compositions used in the present invention provided that such materials do not adversely affect the adhesive properties of the compositions and/or the biocompatibility of the adhesive layer. It is also anticipated that cold blends of two or more silicone pressure-sensitive adhesive compositions may be made to obtain compositions having intermediate properties. For example, up to about 30 weight percent of a modifier such as a silicone pressure-sensitive adhesive composition having 70–90 parts of resin copolymer (A) and 10–30 parts of polydiorganosiloxane (B) having a high adhesion value (e.g., ≧1300 g/inch) can be blended with 70–90 weight percent of a silicone pressure-sensitive adhesive composition of the present invention having 53 parts of resin copolymer (A) and 47 parts of polydiorganosiloxane (B) to improve the adhesion value of the silicone pressure-sensitive adhesive composition (all parts and percentages are by weight based on nonvolatile solids content). It is preferred that the modifier be chemically treated as described above. Use of modifiers containing significant levels of silicon-bonded hydroxyl content can result in an adhesive layer which loses its tack to an unacceptable degree. The modifier need not be a pressure-sensitive adhesive and can comprise from 1 to 100 parts by weight of copolymer (A) and 0 to 99 parts by weight of polydiorganosiloxane (B).

Having described silicone pressure-sensitive adhesive compositions useful in the present invention, one skilled in the art can then construct the improved transdermal drug delivery devices for transdermal delivery delivery of amino-functional drugs using such compositions so that the device can be maintained in contact with the skin of a wearer for a longer period of time than is generally the case for silicone pressure-sensitive adhesives which were not chemically treated as described above, particularly when amino-functional drugs which act as relatively strong bases (pKa≧8.5) are used. Transdermal drug delivery devices of the present invention can also be expected to have a longer shelf life because the adhesive layer does not lose as much of its tack and ability to instantly adhere to the skin upon storage as do untreated compositions of the same type. The same compositions which have not been chemically treated typically lose tack and ability to instantly adhere to the skin with time since in most devices the amino-functional drug begins to migrate from the controlled release means immediately upon construction of the device and thereby contacts the adhesive layer. This is particularly true where the amino-functional drug is a relatively strong base and the silicone pressure-sensitive adhesive composition forms a relatively low tack adhesive and contains about 58 to 65 parts by weight of resin copolymer (A) and 35 to 42 parts by weight of polydiorganosiloxane (B) based on a total of 100 parts by weight of (A) and (B) present in the composition.

The following Examples are illustrative only and should not be construed as limiting the invention which is properly delineated in the appended claims. In the following Examples, all parts and percentages are by weight unless otherwise specified.

Quantitative tack measurements reported therein are performed through use of a POLYKEN™ brand Probe Tack Tester (Testing Machines, Inc., Amityville, N.Y.). Briefly summarized, tack measurements, expressed in units of grams/cm$^2$ of tack, were obtained using a probe velocity of 0.5 cm/sec., a contact pressure of 100 grams/cm$^2$, and contact time of 0.5 seconds. Quantitative adhesion (subsequent adhesion) measurements reported therein were obtained through use of a one inch wide MYLAR® polyester tape which contained a 2 mil (0.051 mm) layer of adhesive (air-dried unless otherwise specified). The tape was adhered to a stainless steel panel with a 4 lb. roller and stripped at a rate of 12 inches/minute at an angle of 180° while attached to a tensile testing machine, with the results expressed in grams per centimeter (cm).

The release values reported were obtained in a manner similar to that used to test adhesion by coating a 2 rail (0.051 mm) film of adhesive (air-dried unless otherwise specified) on a one inch wide release liner (a polyester film coated with a release coating identified as SCOTCH-PAK® 1022 Release Liner, a product of 3M Company, St. Paul, Minn.). The release liner containing the adhesive layer was adhered to a MYLAR® polyester film using a 4 lb. roller and the release liner was stripped at a rate of 40 inches/minute at an angle of 180° while attached to a tensile testing matching, with the results being expressed in grams per centimeter. An average value over the entire panel is recorded and a peak release value is also reported.

The nonvolatile solids content ("N.V.C.") of a material was determined by placing 1.5 g of the material in an aluminum foil dish, 60 mm in diameter and 15 mm deep, and heating the sample for 1 hour at 150° C. in an air-circulating oven. The heated sample was then cooled to room temperature and reweighed to determine the weight of the nonvolatile material (w). The N.V.C., in percent, is equal to 100* w/1.50. The N.V.C. of Resins A1 and A2 were determined by mixing 1.5 g, of the resin with 0.75 g. of a 100 centistoke viscosity trimethylsiloxy-endblocked polydimethylsiloxane fluid in a weighing dish and heating for 2 hours at 150° C. as described above to obtain the N.V.C.

The silicon-bonded hydroxyl content was determined using a lithium aluminum hydride di-N-butyl amide titration based upon the one described by Kellum, et al., and Chem. 39,1623 ff(1967), see also Jorden, and Chem. 30,297 (1964). The acid number was determined by titrating 1.00 g. of the material to a bromcresol purple endpoint using alcoholic KOH and is equal to the number of mg of KOH so used.

The viscosity of a material was determined at 25° C. with a Brookfield® Viscometer Model LVF or RVT using the spindle and speed reported in the Examples. The following ingredients were used in the Examples:

Resin A-1: A xylene solution of a resinous copolymeric siloxane prepared from 45 parts of sodium silicate (41.6° Be) and 20 parts of $Me_3SiCl$ according to the method of the Daudt, et al. patent noted above containing $Me_3SiO_{1/2}$ units and $SiO_{4/2}$ units in a ratio of approximately 0.75:1.0, and N.V.C. typically about 69–71%, an acid number in the range of 0.3 to 1.4, and a viscosity in the range of 10–14 centipoise at 25° C. at 60% N.V.C. in xylene solution, and a silicon-bonded hydroxyl content of about 2.5 weight percent based on a 100% N.V.C. Several different batches of this copolymer were used in the following examples. Resin A-2: A resinous copolymeric siloxane which is the product obtained upon reacting Resin A-1 with a sufficient amount of hexamethyldisilazane to result in a resinous copolymeric siloxane having a silicon-bonded hydroxyl content of about 0.26% based upon 100% nonvolatile solids content. Resin A-2 had a nonvolatile solids content of about 60% in xylene.

Polydiorganosiloxane B-1 ("PDOS B-1"): A polydimethylsiloxane fluid endblocked with silicon-bonded hydroxyl radicals having a viscosity of about 12,000–15,000 centipoise at 25° C. and an N.V.C. minimum of at least 99%.

Polydiorganosiloxane B-2 ("PDOS B-2"): A polyorganosiloxane gum endblocked with silicon-bonded hydroxyl radicals having a viscosity of about 25,000,000 centipoise at 25° C. and a Williams Plasticity Value in the range of 54–60 mils (4.2 g. sample) at about 90% N.V.C., silicon-bonded hydroxyl content of less than about 0.01% based on a 100% nonvolatile solids content. PDOS B-2 was prepared by reaction of 100 parts of a polydimethylsiloxane cyclic trimer with 0.40 parts of a hydroxy-endblocked polydimethylsiloxane fluid having a viscosity of 60–70 centistokes at 25° C. and 0.24 parts of a potassium silanolate catalyst.

During the course of working with the adhesives described herein and in the following Examples, it was found that certain amino-functional drugs affected the SCOTCH-PAK 1022 Release Liner material. As a result, it is believed that interactions between certain drugs and the liner material while the liner was in contact with the adhesive caused changes in the adhesion and release values which were not attributable to the effect of the amino-functional drug on the silicone pressure-sensitive adhesive alone. When transdermal drug delivery devices of the present invention were constructed which contained strongly basic amino-functional drugs, the release liners were found to, after storage, either strongly adhere to the adhesive or else were found to easily peel away from the adhesive.

To obtain a more quantitative measure of the resistance to amino-functional drugs exhibited by the silicone pressure-sensitive adhesives used in the device of the present invention, the viscoelastic properties of films of the silicone pressure-sensitive adhesives described herein were measured under dynamic conditions using a Rheometrics Dynamic Spectrometer Model No. 7700 which is a product of Rheometrics, Inc., Piscataway, N.J. 08854. Samples of films (nominally 1.0 mm. thick) of the silicone pressure-sensitive adhesive were run neat (i.e., as a control with no drug or amine compound added) and after the drug or amine to be tested was mixed into the adhesive and allowed to remain in contact with the adhesive composition before a film of the composition was drawn out as described in the following Examples. It was found that diethanolamine was a strong amine and had a significant effect on some of the silicone pressure-sensitive adhesives; it was employed in some of the following Examples to simulate the effect of a very strongly amino-functional drug on the pressure-sensitive adhesive compositions being tested. The Dynamic Spectrometer was used to measure the following properties of the pressure-sensitive adhesive film being tested at the temperatures noted in the Examples using a % strain of either 1% or 10% while the frequency sweep of the upper platen of the test fixture was started at 1.000E—01 radians/second ("rad/sec") and gradually brought up to 1.000E+02 rad/sec (where, e.g., "1.000E—01"is the well known exponential notation for $1.000 * 10^{-1}$ and is used in that manner in the following Examples): the Elastic (or Storage) Modulus symbolized by G' and reported in dynes/square centimeter ($d/cm^2$); the Viscous (or Loss) Modulus symbolized by G" and reported in $d/cm^2$; the Dynamic Viscosity symbolized by Eta* and reported in poise; the value of G"/G' symbolized by TanDel which has no units; and the torque (in gram-centimeters—"g-cm") measured by a transducer attached to the lower fixed plate of the test fixture holding the sample adhesive film being tested. The test fixture used in the Dynamic Spectrometer employed parallel plates where the adhesive sample to be tested was placed between a fixed lower plate and an oscillating disk upper plate which were separated by a nominal 1.0 mm distance. The Dynamic Spectrometer was operated accordance with directions from the manufacturer.

The following is a brief explanation of the significance of the properties measured by the Dynamic Spectrometer. More detailed treatments of the operation and significance of the properties measured can be found in the literature and can be obtained from the manufacturer. The data in the Examples is presented in tabular form; the data can also be graphically depicted by plotting the values reported for G', G" and Eta* on three decade log/log graph paper where the X-axis depicts the frequency rate in rad/sec and the Y-axis depicts $d/cm^2$ (for G' and G") and Poise (for Eta*). Differences between control and drug- or amine- containing silicone pressure sensitive compositions are readily apparent. The Dynamic Spectrometer shows small changes in modulus, elasticity, hardness and cross-link density of the adhesive being tested. The G' and G" values are indicative of the extent of cross-linking when one sample of an adhesive is compared with the same type of material which has been exposed to an amino-functional material. Thus, if an amino-functional material has acted to condense the free silanol radicals in the silicone pressure-sensitive adhesive composition, the cross-link density is expected to increase and the value of G' and G" tends to increase. Increases in condensation can cause the adhesive to dry out and lose its tack and ability to adhere to the skin. Similarly, the value of Eta* (the Dynamic Viscosity) increases as condensation occurs within the adhesive composition as a result of interaction with the amino-functional material. If no change or only a relatively small change in adhesive properties occurs as a result of exposure to the amino-functional material, then the value of TanDel should remain at about the same level over the period of testing. The value of TanDel is a measure of the stability of the silicone pressure-sensitive adhesive composition. The Dynamic Spectrometer gives a more accurate picture of the effect of the amino-functional drug or amine on the silicone pressure-sensitive adhesive since it measures the direct effect of the drug or amine on the composition without any additional variables being introduced by, e.g., the type of release liner material used to measure adhesion and release values.

EXAMPLE 1

In this example, a precondensation step was employed to prepare a silicone pressure-sensitive adhesive useful in the present invention. 625 g xylene, 655 g of Resin A-1 (73.3% N.V.C.) and 320 g PDOS B-1 were placed in a 3-necked flask equipped with a thermometer, Dean-Stark trap fitted with a water-cooled condenser, a stirring paddle and a heating mantle. Then 8 g of ammonium carbonate (a condensation catalyst) was added to the contents of the flask. The heat was turned on (0 minutes) and the contents of the flask had reached 50° C. after 15 minutes. The temperature had reached 70° C. after 25 minutes and was 80° C. after 40 minutes. After 65 minutes, the temperature was 90° C. and the temperature had reached 105° C. after 90 minutes. After 105 minutes, 48 g hexamethyldisilazane was added and the rate of heating was increased. After 120 minutes, the temperature was 115° C. The heating was terminated after 210 minutes and the contents of the flask were cooled. A total of 14 ml of condensation by-product was collected, a small portion of which appeared to be crystalline in nature and was thought to be ammonium carbonate.

The resulting pressure-sensitive adhesive had an N.V.C. of 61% and a viscosity of 600 centipoise at 25° C. using a Brookfield RVT Viscometer with a #4 spindle at 20 R.P.M. The composition had a ratio of 60 parts of Resin A-1 to 40 parts PDOS B-1 based on 100% N.V.C. An air dried adhesive film of this composition was tacky to the touch, had an adhesion value of 888 g/cm and had a release value of 35.15 g/cm. To check the resistance of this composition to loss of tack in the presence of an amino-functional compound, 0.02 g of a known amino-functional silicon-bonded hydroxyl condensation catalyst, N-(2-aminoethyl)-3-aminopropyltrimethoxysilane, was added to 1.0 g of the above composition (based on 100% N.V.C.) and a film of the catalyzed composition was drawn out and allowed to air dry. The resulting film had retained its tackiness to a light touch after standing overnight at room temperature.

EXAMPLE 2

In this example, a silicone pressure-sensitive adhesive useful in the present invention was prepared in a steam-heated laboratory size (1 quart) Baker-Perkins Mixer Model No. 54089 (a product of Baker-Perkins, Inc., Saginaw, Mich.) using toluene as a solvent. The resulting composition was evaluated for resistance to tack when placed in contact with a primary, a secondary and a tertiary amine.

123 g PDOS B-1 and 241.5 g Resin A-1 (73.3% N.V.C. in xylene solvent) were placed in the Mixer and full vacuum was applied. The steam was turned on and the mixture was heated until distillate was observed. Heating was continued until the mixture had reached about 150° C. and was held at that temperature for one hour to remove the xylene present. The mixture was then cooled to 100° C. with no vacuum and under an inert gas (nitrogen) sweep through the mixture. At about 100° C., 300 g toluene was added and the temperature was brought back up to about 90° C. whereupon 4.5 g of ammonium carbonate was added to the mixture in the mixer. The mixture was maintained at about 90° C. for 1 hour with a nitrogen sweep through the mixture. After 1 hour, 18 grams of hexamethyldisilazane was added to the mixture in the mixer and heating was continued for another hour at 90° C. After 1 hour, 12 g of distilled water was added to the contents of the mixture and allowed to mix for 15 minutes. Full steam was then applied to the heating coils and the mixture was allowed to heat to reflux temperature and the mixture was kept at reflux temperature until the evolution of condensation by-products became constant.

The resulting composition had a ratio of 59 parts of Resin A-1 to 41 parts PDOS B-1 based on 100% N.V.C. An air-dried adhesive film of this composition was tacky to the touch, had an adhesion value of 982 g/cm, a release value of 30.6 g/cm and an N.V.C. of 61%.

To evaluate resistance to loss of tack due to exposure to amino-functional compounds, the following amounts of amine were each stirred into 32.8 g of the above adhesive composition to prepare 3 samples: 1 g n-butyl amine (pKa of 10.77), 2 g N,N-(di-n-butyl)amine and 3 g N,N,N-(tri-n-butyl)amine. Air-dried adhesive films prepared from the samples containing n-butyl amine and N,N,N-(tri-n-butyl)amine were each observed to be tacky to the touch after standing overnight at room temperature. The film prepared using the composition containing N,N-(di-n-butyl)amine was observed to be dry (i.e., had lost its tackiness) to a light touch after standing overnight at room temperature.

EXAMPLE 3

In this Example 3A, a silicone pressure-sensitive adhesive was prepared without a precondensation step using high molecular weight polydimethylsiloxane gum (PDOS B-2). In this example, 395.7 g Resin A-1 (73.3% N.V.C.), 210 g PDOS B-2 (about 90% N.V.C.) and 645 g xylene were mixed together in a flask of the type described in Example 1. After the contents of the flask were mixed well, 27.5 g of hexamethyldisilazane was added, mixed for a short period of time and the contents of the flask were heated to reflux temperature using inert gas (nitrogen) sparging. The contents of the flask were held at reflux temperature for 1.5 hours while condensation by-products were removed through the Dean-Stark trap. After 1.5 hours, the contents of the flask was cooled to room temperature. The resulting chemically-treated composition had a viscosity of 2,400 centipoise, an N.V.C. of 37%, a ratio of 60.5 parts of Resin A-1 to 39.5 parts of PDOS B-2 based on 100% N.V.C. and, assuming the silicon-bonded hydroxyl content of Resin A-1 was about 2.5% and that of PDOS B-2 was very low, the ratio of silicon-bonded hydroxyl radicals to trimethylsiloxy units from the hexamethyldisilazane was 1:0.8. To check the resistance of this composition to loss of tack upon contact with an amine, 1 g of N,N-(di-n-butyl)amine was added to a sufficient amount of the above composition to provide 10 g of 100% N.V.C. adhesive to 1 g of N,N-(di-n-butyl)amine. A film of the composition containing the amine was drawn out, left at room temperature overnight and was observed to be tacky to the touch the next day.

In this Example 3B, a silicone adhesive composition like Example 3A, but having a ratio of Resin A-1 to PDOS B-2 of 58:42 based on 100% N.V.C. and an N.V.C. of 55% (Composition 3B) was tested for loss of tack to the touch by adding various levels of amines. Thus, a control sample film of Composition 3B was drawn out without the addition of any amine, allowed to air dry and stand overnight at room temperature. The next day, the film was observed to be tacky to the touch. Nine individual samples were then prepared by adding the following amounts of amines to 18 g (10 g at 100% N.V.C.) of Composition 3B: 0.1 g, 0.5 g and 1.0 g, respectively, of N-(n-butyl)amine, 0.2 g, 1 g and 2 g of N,N-(di-n-butyl)amine and 0.3 g, 1.5 g and 3.0 g of N,N,N-(tri-n-butyl)amine. As in the control sample, films of each sample were drawn out, allowed to air dry and stand overnight at room temperature. The compositions with 1 g and 2 g of N,N-(di-n-butyl)amine were observed to have lost some tackiness to the touch relative to the control sample with no amine. The rest remained substantially unchanged in tack to the touch relative to the control.

EXAMPLE 4

In this example, a silicone pressure-sensitive adhesive was prepared using $(CF_3CH_2CH_2(CH_3)_2Si)_2NH$ as a chemical treating agent. In this Example, 315 g of a high molecular weight silicon-bonded hydroxyl endblocked polydimethylsiloxane gum having a Williams plasticity in the range of 55–65 mils (4.2 g sample), 566 g Resin A-1 (68% N.V.C.) and 659 g xylene were added to a flask as in Example 1, stirred well and 21 g isopropanol and 21 g distilled water was added to the stirring contents of the flask at room temperature (23° C.). 42 g $(CF_3CH_2CH_2(CH_3)_2Si)_2NH$ was added to the stirring contents of the flask and the contents were heated to reflux temperature. After 60 minutes, condensation by-product evolution was observed (temperature 85° C.). After 220 minutes, the temperature of the contents was 128° C. and 20 ml of condensation by-product had been removed. To obtain a compatible composition, the contents of the flask were held at reflux temperature (128°–134° C.) for another 650 minutes and at that time, the temperature was 134° C. and the contents were cooled. The composition had a viscosity of 4,000 centipoise at 25° C. (Brookfield Model LVF viscometer, speed=6 r.p.m., spindle #4) and had an N.V.C. of 43.5%.

To evaluate the effect of an amine on the tack of this composition, 1% of N,N-(di-n-butyl)amine was added to the composition based upon 100% N.V.C. and two sample films were drawn out, one from the composition containing the amine as a control.

Both films were allowed to air dry overnight at room temperature and were both observed to be equal in tack to the touch after standing overnight at room temperature. Touch tack of each film was evaluated after 3 days at room temperature and each sample appeared to have the same degree of tack to the touch.

EXAMPLE 5

In this Example, a chemically treated copolymeric silicone resin was used to prepare a silicone pressure-sensitive adhesive composition by blending it at room temperature with a high molecular weight silicon-bonded hydroxyl terminated polydimethylsiloxane gum. Thus, 349.16 g Resin A-2, 172 g PDOS B-2 and 143 g xylene were blended together at room temperature until homogenous. Then a total of 900 g of FREON® PCA (trichlorotrifluoroethane) solvent (a product of E. I. duPont de Nemours & Co., Wilmington, DL) was mixed into the blend. The resulting blend had a viscosity of 10,000 centipoise (Brookfield Model RVT, speed=7, spindle=20) at 32% N.V.C. To evaluate the effect of amines on the blend, 5% of N,N-(di-n-butyl)amine was added to a sample of the blend on a 100% N.V.C. basis. After addition of the amine, the viscosity of the sample was 7760 centipoise and reached 8700 centipoise after 3 hours. After 24 hours, the sample containing amine had a viscosity of 10,600 centipoise and, after 6 days, the viscosity was 11,500 centipoise and crystals were observed in the sample.

Pressure-sensitive adhesive films were prepared from a sample of the blend itself (control sample) and the blend containing amine (at 21% N.V.C.) by air drying a film of each composition on the appropriate substrate overnight at room temperature. The control sample had an adhesion value of 769 g/cm and a release value of 20.4 g/cm (some transfer of adhesive was noted). The film from the sample containing amine had an adhesion value of 661 g/cm and a release value of 40 g/cm—some transfer of adhesive was noted and the sample appeared to be elastomeric and not releasing completely. The properties of the adhesive did not appear to be affected to any great extent by the addition of the amine. In view of the transfer observed, use of a peroxide catalyst to cure the adhesive composition appears to be desirable.

EXAMPLE 6

In this example, several different types of silicone pressure-sensitive adhesive were evaluated for resistance to loss of tack to a light touch by a finger on a rating scale where 4=very good tack, 3=good tack, 2=fair tack, 1=poor tack and 0=dry (no tack).

Example 6A was a room temperature blended silicone pressure-sensitive adhesive containing 53 parts of Resin A-1 (based on 100% N.V.C.), 47 parts of PDOS B-2 (based on 100% N.V.C.), 47 parts of xylene, 6 parts of isopropanol and 0.5 parts of a curing catalyst. The curing catalyst ("Catalyst 1") was the reaction product of 115 parts of tetramethylguanidine and 144 parts of 2-ethylhexanoic acid in 1036 parts of xylene.

Example 6B was a room temperature blended silicone pressure-sensitive adhesive containing 53 parts of Resin A-1 (based on 100% N.V.C.), 47 parts PDOS B-2 (based on 100% N.V.C.), 11 parts Resin A-2 (based on 100% N.V.C.), 4 parts isopropanol, 56 parts anhydrous xylene and 0.5 parts Catalyst 1.

Example 6C was made in a manner similar to that described for Example 1, but no endblocking agent was employed and a different solvent was employed. Example 6C was prepared by the following method: 60 parts of Resin A-1 (based on 100% N.V.C.) and 40 parts of PDOS B-1 are heated to 90°–100° C. with nitrogen purging 1.2 g ammonium carbonate is added and the mixture is allowed to condense for one hour at 90°–100° C. A second addition of 1.2 g ammonium carbonate is made and the mixture is stripped of volatiles under vacuum until a temperature of 175° C. is reached. Stripping is continued at 175° C. for about 13 hours until the Williams Plasticity Value of a 2 g sample of the product is at least 140 mils. The product was then cooled and 200 parts of the resulting product is mixed with 200 parts of FREON® PCA. A composition obtained by this method had a viscosity of 9,600 centipoise (Brookfield RVT, spindle=3, speed=5 r.p.m.) at 54.1% N.V.C. This is an example of a low tack adhesive which tends to be rather "dry" (low in tack).

Example 6D was a commercially obtained sample of silicone pressure-sensitive adhesive sold under the name "GE 518" by the General Electric Company, Waterford, N.Y., which was believed to contain a resin copolymer containing trimethylsiloxy and $SiO_{4/2}$ units along with a polydimethylsiloxane which also contained about 2–3 mole percent of diphenylsiloxy units having a viscosity of 86,400 centipoise (Brookfield RVT, spindle #7, speed=20) at an N.V.C. of 53.8% in toluene solvent.

Example 6E was a commercially obtained sample of silicone pressure-sensitive adhesive composition sold under the name "GE 529" by the General Electric Company which was believed to contain a resin copolymer containing trimethylsiloxy units and $SiO_{4/2}$ units along with a polydimethylsiloxane having an N.V.C. of about 55% in toluene solvent. This composition was a low tack adhesive which was a rather "dry" adhesive.

Example 6F was a commercially obtained sample of silicone pressure-sensitive adhesive composition sold under the name "GE 595" by the General Electric Company which was believed to contain a resin copolymer containing trimethylsiloxy units and $SiO_{4/2}$ units along with a polydimethylsiloxane having an N.V.C. of about 55% in xylene solvent.

The manner in which Examples 6D–6F were manufactured was not ascertainable nor was such information readily available from the manufacturer.

Films of these compositions along with a composition having the formulation used in Example 3B were drawn out and air-dried overnight at room temperature and were evaluated for adhesion, release and initial tack to the touch (control samples). Then 5% N,N-(di-n-butyl)amine was added to each composition based upon 100% N.V.C. of each composition, a film was drawn out and air-dried overnight and tack to the touch was evaluated relative to the control sample. The results are reported below:

| | Control | | | |
|---|---|---|---|---|
| Example | Adhesion (g/3.5 cm) | Release (g/cm) | Tack* | 5% Amine Tack* |
| 6A | 553 | 145 | 3+ | 3+ |
| 6B | 520 | 164 | 3 | 2– |
| 6C | 636 | 14 | 1 | 0 |
| 6D | 670 | 345 | 4 | 4 |
| 6E | 1127 | 14 | 0+ | 0 |
| 6F | 698 | 100 | 3 | 3 |
| 3B | 450 | 60 | 3 | 3 |

*Qualitative Finger Tack
4 = very good,
3 = good,
2 = fair,
1 = poor,
0 = dry (no tack).

The tack of Example 6A did not appear to be affected by the addition of amine while Example 6B did lose tack. Examples 6C and 6E which were both "dry" adhesives initially both lost their tack to the touch and became dry. Examples 6D and 6F were high tack adhesives and retained their tack as did the chemically treated Example 3A.

EXAMPLE 7

In this Example, several chemically treated silicone pressure-sensitive adhesive compositions were prepared for use in a study along with some of the compositions of Example 6 involving contact with 3 amino-functional drugs.

Example 7A had the following formulation: 53 parts Resin A-1 (based on 100% N.V.C.), 47 parts PDOS B-2 (based on 100% N.V.C.), 150 parts xylene, 5.5 parts hexamethyldisilazane, 2.8 parts water and 1.3 parts isopropanol. The procedure used involved charging all of the above ingredients except the hexamethyldisilazane into a kettle with a stirring paddle and reflux condenser and stirring until the contents are homogeneous. The hexamethyldisilazane is added to the stirring contents and the contents are heated to reflux temperature for 3 hours while condensation by-products, alcohol and water are removed azeotropically. After three hours, some of the xylene solvent is stripped out until the N.V.C. of the mixture is about 55%.

Example 7A was found to have a viscosity of 37,300 centipoise (Brookfield RVT, spindle=7, speed=20).

Example 7B was prepared by taking a silicone pressure-sensitive adhesive composition prepared by the method used in Example 7A and stripping out the xylene solvent by placing the composition in a larger 2½ gallon mixer of the type used in Example 2, applying full vacuum (with nitrogen gas sweep) and gradually heating the stirring contents to 150° C. over a period of 100 minutes while the xylene was being removed. The resulting stripped product had an N.V.C. content of 99.2%. The stripped product was cooled and a sufficient amount of FREON® PCA solvent was slowly blended in to result in a composition having a viscosity of 5260 centipoise (Brookfield RVT, spindle=#3, speed=10 r.p.m.) at about 28% N.V.C.

Example 7C was prepared in a manner similar to that used for Example 7A as follows: 58 parts of Resin A-1 (based on 100% N.V.C.), 42 parts of PDOS B-1 and a total of 66 parts of xylene (including the xylene present in Resin A-1), 1.8 parts water and 6 parts isopropanol were charged to the mixer using nitrogen sparging and mixed well at room temperature. The mixture was heated to 80° C., 1.2 parts ammonium carbonate was added and the contents were held at 80° C. for an additional hour. The contents were cooled to about 60° C. and 1.8 parts water and 6 parts isopropanol (to replace that which was lost during the previous step) along with 6 parts hexamethyldisilazane were added and the contents were heated to reflux temperature (about 130° C.) and held at reflux temperature for 3 hours. After 3 hours, the xylene solvent was stripped from the contents of the kettle using a nitrogen sweep and vacuum to remove as much xylene as possible and cooled. A sufficient amount of FREON® PCA solvent was added after the stripping process to reduce the N.V.C. of the contents to 41%. The resulting composition had a viscosity of 200 centipoise (Brookfield RVT, Spindle #4, 20 r.p.m.).

Example 7D was prepared in a large 2½ gallon mixer of the type used in Example 2 by adding 2457 g Resin A-1 (73.3% N.V.C. in xylene), 1200 g PDOS B-1, and 2344 g xylene to the mixer and stirring well at room temperature. The contents were heated to 90° C. with nitrogen gas sparging, 36 g of ammonium carbonate was added to the contents and the contents of the mixer were held at 90° C. for one hour. After one hour, a second addition of 36 g of ammonium carbonate was made and the contents were held at 90° C. for an additional hour. The contents were then cooled to about 60° C. and 54 g water, 180 g isopropanol and 180 g hexamethyldisilazane were added to the contents of the mixer. The contents of the mixer were heated to reflux and held for 3 hours. The contents of the mixer were then stripped of volatile materials under vacuum using a slow nitrogen sweep allowing the temperature to rise to 150° C. until the N.V.C. of the contents was greater than 98%. The contents were cooled and a sufficient amount of FREON® PCA was added to the contents with mixing to reduce the N.V.C. of the contents to 45%. The resulting composition had a viscosity of 1,700 centipoise (Brookfield RVT, spindle #4. speed=20 r.p.m.) at 44.1% N.V.C.

EXAMPLE 8

Samples of the compositions of Examples 6A, 6C, 6D, 7A, 7B, 7C and 7D were evaluated for the effect of amino-functional drugs on tack, adhesion, release and viscosity by adding each of the following drugs (based on 100% N.V.C. of the composition) to each composition: 5% of phenylpropanolamine (pKa=9.2), 2½% of theophylline PKa=8.8) and 2½% of propranolol (pKa=9.4). The compositions of Examples 6A, 6C and 6D were used for comparative purposes and the other examples describe compositions falling within the scope of this invention. A control sample (no amino-functional drug added) was included for each drug being evaluated. Films of each composition were drawn out, allowed to air dry and then laminated with a release liner of SCOTCH-PAK® 1022 Release Liner. The laminated films and samples of each composition for viscosity measurements were stored at room temperature. Testing was done initially, and after 3 days, 7 days, 1 month, 2 months, 3 months and 4 months. The results are reported in Table I (tack values), Table II (viscosity values), Table III (adhesion values) and Table IV (release values). The viscosity was measured at room temperature using a Brookfield Model RVT Viscometer wherein spindle #7 at speed 20 r.p.m. was used for viscosities in excess of about 20,000 centipoise and spindle #3, 4 or 5 were used at speed=20 r.p.m. for the other samples depending on the viscosity of the material being tested. Of the compositions tested, the amino-functional drugs had the greatest effect on Example 6C and caused the film to rapidly lose its tack and, in the case of two of the drugs, a significant increase in viscosity.

Example 7D was similar to Example 6C in composition and two of the drugs caused a pronounced loss of tack value. This result is unexplained since batches using the same formulation had been found to be resistant to the loss of tack when evaluated as an adhesive layer on transdermal drug delivery devices for amino-functional drugs.

Example 7C employed 2 parts less of Resin A-1 than did Example 7D. It appeared to be more resistant to the loss of tack than Example 7D and greatly more resistant to loss of tack than Example 6C. Theophylline and propranolol appeared to have the greatest effect on the release values of Examples 7C and 7D.

Theophylline and propranolol had the greatest effects on the tack of Example 6A while only an initial change in tack was noted for Example 6D upon exposure to theophylline. Exposure to the drugs phenylpropanolamine and theophylline caused the viscosity of Example 6A to increase while the other drug caused a loss in viscosity. The viscosity of Example 6D remained relatively stable in the presence of the drugs tested. Theophylline had the greatest effect on the release values of Examples 6A and 6D. The other drugs affected the release values of those samples somewhat. Adhesion values remained relatively constant upon exposure to the drugs.

Finally, Example 7A remained tacky upon exposure to the drugs with propranolol having the greatest initial effect on tack. The viscosity of each sample remained fairly constant. Phenylpropanolamine had the greatest effect on adhesion and release. Theophylline had the greatest effect on release values.

Except for Example 7D, Examples 7A, 7B and 7C retained a reasonably good amount of their tack value after exposure to amino-functional drugs, unlike Example 6C which was a "dry", low tack adhesive. Example 6A was affected more by the drugs than was Example 6D, but both retained a reasonable amount of tack.

During the course of this evaluation, it was noted that some of the drug tended to come to the surface of the film being tested where it could have affected the property being tested (e.g., tack). This may account for some of the variability in values reported. Another variable could be the unexpected effect of the drugs on the release liner. When drug interacted with the release liner, the adhesion values were lower than would normally be expected. Some of the drugs (which are solid compounds) were not entirely compatible with the compositions at the relatively high levels used, and some of them may not have been exposed to all of the drug (drug was noticed at the top of some of the solution viscosity samples during storage). The films also contained some particles of drug and that may have affected measurement of the film properties. Chemical effects visible as significant viscosity increases or substantial loss of tack value are more indicative of changes due to the drug itself than variation in release which can be due to drug interactions with the release liner (unless the adhesive itself was observed to have degraded).

TABLE I

| | | Tack Values (g/cm$^2$) | | | | | | |
|---|---|---|---|---|---|---|---|---|
| Ex. # | DRUG* | Initial | 3 Days | 7 Days | 1 Month | 2 Months | 3 Months | 4 Months |
| 6A | CONTROL | 503 | 477 | 573 | 547 | 98 | 627 | 628 |
| 6A | PPA | 470 | 293 | 473 | 263 | 398 | 460 | 548 |
| 6A | THEO | 247 | 487 | 343 | 177 | 353 | 267 | 200 |
| 6A | PROPR | 77 | 100 | 138 | 303 | 415 | 627 | 480 |
| 6C | CONTROL | 90 | 90 | 90 | 73 | 308 | 328 | 379 |
| 6C | PPA | 70 | 53 | 90 | 0 | 123 | 197 | 260 |
| 6C | THEO | 8 | 5 | 0 | 7 | 0 | 0 | 0 |
| 6C | PROPR | 1 | 0 | 10 | 0 | 0 | 8 | 1 |
| 6D | CONTROL | 502 | 495 | 437 | 537 | 585 | 565 | 495 |
| 6D | PPA | 400 | 310 | 433 | 590 | 498 | 603 | 370 |
| 6D | THEO | 107 | 210 | 457 | 500 | 450 | 422 | 180 |
| 6D | PROPR | 523 | 490 | 303 | 458 | 585 | 648 | 390 |
| 7A | CONTROL | 300 | 307 | 270 | 283 | 142 | 353 | 338 |
| 7A | PPA | 433 | 493 | 460 | 493 | 453 | 560 | 565 |
| 7A | THEO | 403 | 397 | 430 | 423 | 527 | 588 | 428 |
| 7A | PROPR | 263 | 307 | 250 | 435 | 432 | 738 | 577 |
| 7D | CONTROL | 640 | 823 | 757 | 673 | 600 | 878 | 900 |
| 7B | PPA | 433 | 743 | 760 | 570 | 573 | 598 | 880 |
| 7B | THEO | 407 | 420 | 540 | 247 | 320 | 701 | 190 |
| 7D | PROPR | 238 | 313 | 197 | 405 | 513 | 673 | 703 |
| 7C | CONTROL | 783 | 907 | 780 | 823 | 700 | 778 | 893 |
| 7C | PPA | 633 | 743 | 653 | 450 | 478 | 578 | 792 |
| 7C | THEO | 253 | 257 | 167 | 293 | 277 | 513 | 131 |
| 7C | PROPR | 275 | 180 | 212 | 170 | 462 | 412 | 317 |
| 7D | CONTROL | 260 | 320 | 303 | 343 | 427 | 388 | 527 |
| 7D | PPA | 67 | 50 | 173 | 43 | 262 | 257 | 360 |
| 7D | THEO | 10 | 13 | 5 | 2 | 5 | 0 | 0 |
| 7D | PROPR | 48 | 8 | 47 | 5 | 25 | 87 | 2 |

*PPA = phenylpropanolamine;
THEO = theophylline;
PROPR = propranolol

TABLE II

| | | Viscosity (centipoise) | | | | | | |
|---|---|---|---|---|---|---|---|---|
| Ex. # | DRUG* | Initial | 3 Days | 7 Days | 1 Month | 2 Months | 3 Months | 4 Months |
| 6A | CONTROL | 86600 | 100000 | 100000 | 104000 | 120000 | 133000 | 160000 |
| 6A | PPA | 160000 | 140000 | 120000 | 138000 | 154000 | 145000 | 194600 |
| 6A | THEO | 120000 | 138000 | 156000 | 126000 | 144000 | 123000 | 156000 |
| 6A | PROPR | 143000 | 143000 | 122000 | 124400 | 110000 | 119000 | 126000 |
| 6C | CONTROL | 450 | 500 | 520 | 500 | 560 | 650 | 700 |
| 6C | PPA | 2300 | 1200 | 650 | 5250 | 8000 | 9400 | 15000 |
| 6C | THEO | 550 | 1000 | 1400 | GELLED | — | — | — |
| 6C | PROPR | 400 | 460 | 450 | 300 | 260 | 250 | 250 |
| 6D | CONTROL | 86400 | 86000 | 97000 | 100000 | 109500 | 126000 | 134000 |
| 6D | PPA | 86000 | 90000 | 93000 | 103000 | 114000 | 125000 | 134000 |
| 6D | THEO | 90000 | 97000 | 98400 | 120000 | 130000 | 115000 | 106000 |

TABLE II-continued

| | | Viscosity (centipoise) | | | | | | |
|---|---|---|---|---|---|---|---|---|
| Ex. # | DRUG* | Initial | 3 Days | 7 Days | 1 Month | 2 Months | 3 Months | 4 Months |
| 6D | PROPR | 88000 | 85000 | 85500 | 110000 | 94000 | 101000 | 102000 |
| 7A | CONTROL | 37300 | 39000 | 40000 | 41200 | 43000 | 49200 | 51600 |
| 7A | PPA | 39000 | 39000 | 40500 | 40000 | 45400 | 48000 | 53000 |
| 7A | THEO | 40000 | 45000 | 48000 | 43200 | 52000 | 54000 | 60000 |
| 7A | PROPR | 40000 | 41300 | 42300 | 38800 | 43000 | 40000 | 41500 |
| 7B | CONTROL | 5260 | 6260 | 6400 | 5880 | 7000 | 8000 | 8800 |
| 7B | PPA | 6400 | 6500 | 8800 | 7800 | 11250 | 10900 | 22000 |
| 7B | THEO | 6550 | 8400 | 8400 | 7400 | 8600 | 10740 | 10920 |
| 7B | PROPR | 6500 | 7000 | 4200 | 7600 | 8000 | 12000 | 130000 |
| 7C | CONTROL | 150 | 150 | 200 | 870 | 1000 | 1160 | 1880 |
| 7C | PPA | 100 | 800 | 200 | 250 | 250 | 300 | 400 |
| 7C | THEO | 200 | 200 | 300 | 370 | 350 | 220 | 500 |
| 7C | PROPR | 200 | 200 | 200 | 200 | 260 | 1750 | 350 |
| 7D | CONTROL | 360 | 400 | 400 | 6850 | 9800 | 12800 | 17260 |
| 7D | PPA | 4250 | 1000 | 420 | 2350 | 4300 | 5800 | 6400 |
| 7D | THEO | 400 | 1000 | 1200 | 3440 | 2800 | GELLED | GELLED |
| 7D | PROPR | 990 | 2300 | 600 | 720 | 1180 | 260 | 350 |

*PPA = phenylpropanolamine;
THEO = theophylline;
PROPR = propranolol

TABLE III

| | | Adhesion Values (g/cm) | | | | | | |
|---|---|---|---|---|---|---|---|---|
| Ex. # | DRUG* | Initial | 3 Days | 7 Days | 1 Month | 2 Months | 3 Months | 4 Months |
| 6A | CONTROL | 368 | 392 | 324 | 426 | 523 | 430 | 421 |
| 6A | PPA | 283 | 275 | 286 | 382 | 523 | 510 | 424 |
| 6A | THEO | 150 | 212 | 211 | 166 | 303 | 161 | 248 |
| 6A | PROPR | 139 | 184 | 243 | 499 | 385 | 388 | 293 |
| 6C | CONTROL | 656 | 668 | 708 | 634 | 745 | 602 | 644 |
| 6C | PPA | 501 | 621 | 697 | 218 | 489 | 542 | 342 |
| 6C | THEO | 63 | 214 | FAIL | FAIL | 229[4] | FAIL | FAIL |
| 6C | PROPR | 332 | 290 | 246 | 266 | 442 | 259 | 397 |
| 6D | CONTROL | 488 | 307 | 413 | 494 | 327 | 383 | 463 |
| 6D | PPA | 335 | 451 | 435 | 554 | 340 | 379 | 437 |
| 6D | THEO | 270 | 438[1] | 173[1] | 250 | 395 | 363 | 305 |
| 6D | PROPR | 498 | 464 | 370 | 505 | 483 | 429 | 791 |
| 7A | CONTROL | 159[1] | 332 | 335 | 587 | 698 | 840 | 777 |
| 7A | PPA | 1196[1] | 1198 | 963 | 847 | 1161 | 990 | 864 |
| 7A | THEO | 669 | 375 | 263 | 297 | 366 | 212 | 248 |
| 7A | PROPR | 255 | 343 | 364 | 602 | 557 | 436 | 514 |
| 7B | CONTROL | 606 | 517 | 637 | 531 | 591 | 540 | 397 |
| 7B | PPA | 441 | 426 | 524 | 512 | 551 | 537 | 465 |
| 7B | THEO | 251 | 288 | 272 | 287 | 268 | 297 | 222 |
| 7B | PROPR | 368 | 423 | 490 | 468 | 453 | 407 | 315 |
| 7C | CONTROL | 966[2] | 802[2] | 866 | 750 | 857 | 872 | 842 |
| 7C | PPA | 626 | 651 | 700 | 442 | 811 | 937 | 685 |
| 7C | THEO | 308 | 318 | 236 | 419 | 321 | 275 | 250 |
| 7C | PROPR | 588 | 541 | 512 | 345 | 586 | 536 | 419 |
| 7D | CONTROL | 617 | 629 | 620 | 640 | 713 | 651 | 579 |
| 7D | PPA | 275 | 438 | 442 | 456 | 383 | 438 | 406 |
| 7D | THEO | 53 | 364 | FAIL | FAIL | 138[4] | FAIL | FAIL |
| 7D | PROPR | 500 | 232 | 139 | 342[3] | 317 | 462 | 374 |

*PPA = phenylpropanolamine;
THEO = theophylline;
PROPR = propranolol
[1]Stringy - some transfer of adhesive noted.
[2]Some transfer of adhesive noted.
[3]Adhesive losing its integrity.
[4]Retested even though film integrity was lost (failure).

TABLE IV

| Ex. # | DRUG* | Release Values (g/cm)[1] Initial | 3 Days | 7 Days | 1 Month | 2 Months | 3 Months | 4 Months |
|---|---|---|---|---|---|---|---|---|
| 6A | CONTROL | 24(48) | 17(27) | 17(24) | 16(23) | 10(15) | 13 | 10 |
| 6A | PPA | 33(47) | 20(45) | 19(28) | 30(39) | 43(65) | 48 | 54 |
| 6A | THEO | 106(154) | 262(306)[3] | 314(469)[4] | 95(129) | 132(205) | 84 | 89 |
| 6A | PROPR | 21(30) | 38(65) | 41(51) | 126(186) | 179 | 186 | 114 |
| 6C | CONTROL | 8.8(19) | 4.2(12) | 3.9(9.1) | 7.0(13) | 3.9(9.8) | 2 | 1 |
| 6C | PPA | 4.2(11) | 3.2(15) | 1.0(9.1) | 1.4(12) | 4.2(9.1) | 3 | 18 |
| 6C | THEO | 126(267)[2] | 57(185)[2] | 42(194)[2] | 193(382) | 161(282) | 127 | 102 |
| 6C | PROPR | (4) | 7.7(36) | 81(300) | 58(196) | 21 | 18 | 6 |
| 6D | CONTROL | 115(166) | 46(48) | 151(181) | 162 | 92 | 110 | 147 |
| 6D | PPA | 81(100) | 135(150) | 130(203) | 191 | 106 | 158 | 160 |
| 6D | THEO | 271(361) | 463(634) | 216(299) | 120 | 217 | 186 | 156 |
| 6D | PROPR | 116(155) | 187(253) | 129(197) | 196 | 129 | 129 | 229 |
| 7A | CONTROL | 145(341) | 24(115) | 185(368) | 321(628) | 68(366) | 96 | 185 |
| 7A | PPA | 15(22) | 21(44) | 9.8(18) | 13(35) | 14(38) | 20 | 15 |
| 7A | THEO | 128(184) | 173(209) | 124(158) | 50(72) | 83(115) | 40 | 40 |
| 7A | PROPR | 48(70) | 68(113) | 22(38) | 63(100) | 38 | 25 | 43 |
| 7B | CONTROL | 46(21) | 18(25) | 19(28) | 14(20) | 12(16) | 15 | 13 |
| 7B | PPA | 20(27) | 20(30) | 20(27) | 19(27) | 16(20) | 17 | 16 |
| 7B | THEO | 123(175) | 184(224) | 152(194) | 67(92) | 88(122) | 104 | 101 |
| 7B | PROPR | 15(36) | 38(56) | 67(95) | 52(108) | 83 | 96 | 168 |
| 7C | CONTROL | 30(41) | 23(30) | 27(38) | 21(39) | 24(36) | 18 | 15 |
| 7C | PPA | 19(29) | 11(18) | 14(21) | 10(16) | 19(28) | 15 | 12 |
| 7C | THEO | 181(234) | 279(323) | 280(380)[4] | 135(191) | 170(220) | 100 | 156 |
| 7C | PROPR | 30(50) | 84(137) | 89(225) | 208(297) | 90 | 139 | 168 |
| 7D | CONTROL | 7.0(11) | 4.2(9.5) | 8.8(14) | 4.2(9.8) | 4.9(7.0) | 5 | 4 |
| 7D | PPA | 34(46) | 41(59) | 10(22) | 8.8(15) | 9.1(15) | 7 | 5 |
| 7D | THEO | 239(407)[2] | 167(313)[2] | 283(398)[2] | 231(344) | 164(322) | 150 | 127 |
| 7D | PROPR | 13(58) | 52(161) | 314(425) | 184(335)[3] | 65 | 132 | 141 |

*PPA = phenylpropanolamine;
THEO = theophylline;
PROPR = propranolol
[1]In table, the average value over the entire sample is reported and peak value is recorded in parentheses.
[2]Poor release noted.
[3]Elastomeric, film losing its integrity.
[4]Cheesy appearance.

EXAMPLE 9

To evaluate the results obtained with the composition of Example 7D, another batch of that type of composition was prepared as follows: Example 9A was made by combining three smaller batches of silicone pressure-sensitive adhesive compositions which were prepared as follows where the average ratio of PDOS B-1 to Resin A-1 was 41:59 instead of the 40:60 ratio used in Example 7D. More PDOS B-1 was used because the Resin A-1 batches used produced higher plasticity values when they were condensed in a test run with PDOS B-1 than that obtained in Example 7D. This ratio was used to obtain an adhesive composition which is more consistent with the properties obtained with Example 7D. A total of 67 parts of xylene per 100 parts of total Resin A-1 and PDOS B-1 was used to obtain a product having a nonvolatile solids content of about 60%. The procedure followed was one wherein the PDOS B-1, Resin A-1 (at about 67% nonvolatile content in xylene) and remaining xylene (to obtain 60% nonvolatile content) are mixed together for 30 minutes and that mixture is heated to 90°–100° C. whereupon a flow of anhydrous ammonia (10–20 cc/minute/pound of nonvolatile content) is started through the stirring mixture. The mixture is held at 90°–100° C. for two hours. The 6 parts of hexamethyldisilazane, 6 parts of isopropanol and 1.8 parts of water (each based on 100 parts of total PDOS B-1 and Resin A-1) are added to the mixture (cooled to permit the addition) and then the mixture is heated to reflux (about 140° C.) and is held at reflux for 3 hours. After 3 hours, the mixture is stripped to about 70% nonvolatile solids content. Three different batches of compositions prepared by this procedure were blended together in a Baker-Perkins-type mixer and were stripped to greater than 98% nonvolatile content using full steam pressure and vacuum at 27 inches Mercury for two and one-half hours (top temperature was about 150° C.). The stripped composition was cooled and redissolved in FREON™ PCA. The nonvolatile content of the resulting composition (Example 9A) was found to be 35.0%.

To Example 9A was added 1% of aminophylline (Example 9B), 1% propranolol (Example 9C), 1% phenylpropanolamine (Example 9D), and 1% diethanolamine (Example 9E). The diethanolamine was included as an example of a strong amino-functional compound. The samples were stored at 51° C. in sealed jars and the adhesion values, release values, tack values and viscosity obtained after one day ("t0") and after six weeks ("t6") of aging at that temperature are tabulated below:

| Example | Adhesion* (g/cm) | Release* (g/cm) | Tack* (g/cm2) | Viscosity* (centipoise) |
|---|---|---|---|---|
| 9A | 559/557 | 5/3 | 232/190 | 400/400 |
| 9B | 164/174 | 269/157 | 158/40 | 500/650 |
| 9C | 326/327 | 8/28 | 175/140 | 700/gel |
| 9D | 374/354 | 7/6 | 375/186 | 600/750 |
| 9E | 59/13 | 68/1 | 0/0 | 400/350 |

*The first figure is t0 value and the second is t6

The Dynamic Spectrometer testing results obtained after six weeks aging at 51° C. are tabulated in Table V. The aged samples were tested in the Dynamic Spectrometer in air at 30° C. and a strain of 1%. Based on the above tabulation, the control Example 9A appeared to be quite stable in all properties measured. After addition of the drug or amine, differences from the control were apparent even after 1 day at 51° C. The adhesion values for Examples 9B–9D changed relative to the control Example 9A at t0 and remained relatively constant six weeks later. Example 9C remained relatively constant in tack value although the composition almost doubled in viscosity and gelled after exposure to propranolol for 6 weeks at 51° C. Example 7D gelled after exposure to theophylline as shown in Table II, but that composition actually decreased in viscosity with time when exposed to propranolol. The data in Table V shows that Examples 9A and 9C were almost identical in the measured values of G', G", Eta* and TanDel indicating that the adhesion and release values most likely reflect changes which are not due to the effect of the drug on the adhesive composition itself. The dynamic viscosity (Eta*) for Example 9C is almost identical to that for the control even though the measured solution viscosity values shown above differ and Example 9C appears gelled after six weeks of aging. The same is true when the data obtained for Example 9D in Table V is compared with that found for Example 9A. Since the Dynamic Spectrometer data measures the properties of a solvent-free film of the adhesive itself without a need for the use of a release liner (the adherence of which could be affected by the presence of drug between the liner and the surface of the adhesive), the Dynamic Spectrometer data shows that Example 9A is quite resistant to the effect of propranolol and phenylpropanolamine.

The tack values of Examples 9B and 9E changed substantially relative to control Example 9A with diethanolamine causing the greatest loss of tack in the shortest period of time. This is supported by the data obtained in Table V wherein the value of G' for Example 9B has increased approximately by one order of magnitude and that for Example 9E by almost two orders of magnitude relative to G' for Example 9A. Similar effects on the Dynamic Viscosity of those Examples relative to the control are evident from Table V. Thus, Example 9B still retains some tack after aging, but not to the extent exhibited by Examples 9C and 9D while Example 9E shows that the adhesive composition tested here is not very resistant to the effects of the strongly amino-functional diethanolamine. The solution viscosity reported above for Examples 9B and 9E appears to have changed moderately for the former and very little for the latter, yet the tack values are quite different from Example 9A. The Dynamic Spectrometer appears to provide a more valid indication of which silicone pressure-sensitive adhesive compositions are affected by amino-functional compounds placed in contact with the adhesives than adhesion values, release values or solution viscosity data.

TABLE V

| | Drug/Amine | Example | | | | |
|---|---|---|---|---|---|---|
| Property | Frequ. (rad/sec) | 9A CTRL.* | 9B AMINO* | 9C PROPR* | 9D PPA* | 9E DEA* |
| G' | 0.1 | 1.1E5 | 7.3E6 | 1.2E5 | 1.9E5 | 3.6E7 |
| (d/cm$^2$) | 1.0 | 8.6E5 | 1.9E7 | 9.6E5 | 1.4E6 | 3.9E7 |
| | 10 | 4.9E6 | 2.9E7 | 5.4E6 | 7.0E6 | 4.1E7 |
| | 100 | 1.5E7 | 3.6E7 | 1.6E7 | 1.8E7 | 4.3E7 |
| G" | 0.1 | 2.8E5 | 6.2E6 | 2.9E5 | 4.4E5 | 4.0E6 |
| (d/cm$^2$) | 1.0 | 1.5E6 | 7.7E6 | 1.7E6 | 2.2E6 | 2.4E6 |
| | 10 | 4.9E6 | 6.0E6 | 5.3E6 | 6.1E6 | 1.7E6 |
| | 100 | 8.4E6 | 5.4E6 | 8.7E6 | 8.8E6 | 3.1E6 |
| Eta* | 0.1 | 3.0E6 | 9.6E7 | 3.1E6 | 4.8E6 | 3.4E8 |
| (poise) | 1.0 | 1.7E6 | 2.1E7 | 1.9E6 | 2.6E6 | 3.9E7 |
| | 10 | 7.0E5 | 3.0E6 | 7.5E5 | 9.2E5 | 4.1E6 |
| | 100 | 1.7E5 | 3.7E5 | 1.8E5 | 2.0E5 | 4.3E5 |
| TanDel | 0.1 | 2.5 | 0.85 | 2.4 | 2.3 | 0.12 |
| | 1.0 | 1.8 | 0.40 | 1.7 | 1.6 | 0.063 |
| | 10 | 1.0 | 0.20 | 0.98 | 0.87 | 0.041 |
| | 100 | 0.56 | 0.15 | 0.54 | 0.48 | 0.072 |
| Torque | 0.1 | 9.2 | 293 | 10 | 15 | 1050 |
| (g/cm) | 1.0 | 53 | 629 | 58 | 78 | 1179 |
| | 10 | 216 | 889 | 234 | 288 | 1170 |
| | 100 | 410 | 666 | 421 | 457 | 727 |

*CTRL = Control;
AMINO = Aminophylline;
PROPR = Propranolol;
PPA = Phenylpropanolamine;
DEA = Diethanolamine

EXAMPLE 10

In this Example, a silicone pressure-sensitive adhesive composition was prepared in the manner described for Example 9A with the exceptions that (A) the formulation used contained 40.5 parts PDOS B-1, 59.5 parts Resin A-1 (on a nonvolatile solids content basis), a total of 65 parts of xylene (to obtain 60% nonvolatile solids content), 8.6 parts hexamethyldisilazane and 1.75 parts water, (B) the mixture was held for 1 hour at 90°–100° C. after the hexamethyldisilazane and water were added before heating to reflux was commenced and (C) the composition was evaluated as a 70% solution in xylene rather than using the solvent stripping process of Example 9A (hereinafter "Example 10A"). The ratio of end-blocking silyl radicals to silicon-bonded hydroxyl radicals was estimated to be about 1.5:1.0 which is higher than in Example 9A. To test the resistance of Example 10A to diethanolamine, 2% by weight of diethanolamine (based on the nonvolatile solids content) was added to a sample of Example 10A (hereinafter "Example 10B"). Samples of Example 10A and of Example 10B were placed in a forced air oven at 150° C. in an aluminum weighing dish for a period of 16 hours to simulate accelerated aging of each sample. Dynamic Spectrometer data for each sample was obtained on each film from the weighing dish and the results are reported in Table VI.

To determine if the resistance of Example 10A to diethanolamine could be improved by further removing silicon-bonded hydroxyl content, 409.7 g. of Example 10A was charged to a three-necked flask equipped with a stirrer, thermometer, heating mantle, and a water-cooled overhead condenser. 124.93 g. xylene was charged to the flask and the contents of the flask were heated to 140° C. at which time a small mount of water was collected through the condenser. The contents of the flask were cooled to less than 50° C. and 16.0 g. hexamethyldisilazane was added to the flask. The temperature was 68° C. and at that point, 3 drops of trifluoroacetic acid was added to the contents. The contents of the flask was held at between 66° and 72° C. for 5 hours to permit the hexamethyldisilazane to react with any residual silicon-bonded hydroxyl radicals present in the composition. After 5 hours, 3.7 g. isopropanol and 17.8 g. distilled water were added to the contents of the flask and the contents were heated to reflux temperature. After 169.3 g. of volatile material was collected through the overhead condenser, the contents of the flask were cooled to room temperature. This product is hereinafter referred to as Example 10C. Example 10A was found to have a silicon-bonded hydroxyl content of 0.72% and that of Example 10C was found to be 0.23% indicating that the silicon-bonded hydroxyl content was reduced by this procedure. The resistance of Example 10C to diethanolamine was evaluated in the same manner as done with Examples 10A and 10B where the sample containing 2% diethanolamine was designated "Example 10D". Dynamic Spectrometer data for each of Examples 10C and 10D after 16 hours aging at 150° C. were obtained and are reported in Table VI. The Dynamic Spectrometer data was obtained at a sample temperature of 30° C. at a 1% strain setting.

Table VI shows that the additional endblocking procedure performed on Example 10A to produce Example 10C did not substantially change the properties of the resulting composition. Example 10C was found to be a drier adhesive to the touch (i.e., not as tacky) than was Example 10A. The magnitude of the difference in properties reported in Table VI between Examples 10A and 10B is larger than that observed between Examples 10C and 10D which indicates that Example 10C was more resistant to the effect of amino-functional diethanolamine than was Example 10A. A film of Example 10B was found to be dry to the touch while a film of Example 10D was still found to be tacky to the touch. Thus, Example 10C was more resistant to amino-functional compounds than was Example 10A.

TABLE VI

| Property | Frequ. (rad/sec) | Example 10A | 10B | 10C | 10D |
|---|---|---|---|---|---|
| G' | 0.1 | 1.6E5 | 9.3E6 | 1.3E5 | 1.1E6 |
| (d/cm$^2$) | 1.0 | 1.4E6 | 2.1E7 | 1.3E6 | 6.3E6 |
| | 10 | 7.9E6 | 2.9E7 | 8.0E6 | 1.7E7 |
| | 100 | 2.0E7 | 3.5E7 | 2.1E7 | 2.8E7 |
| G" | 0.1 | 4.6E5 | 6.7E6 | 4.2E5 | 1.9E6 |
| (d/cm$^2$) | 1.0 | 2.5E6 | 6.9E6 | 2.4E6 | 5.7E6 |
| | 10 | 6.8E6 | 5.0E6 | 7.2E6 | 7.5E6 |
| | 100 | 9.0E6 | 4.9E6 | 9.5E6 | 7.1E6 |
| Eta* | 0.1 | 4.9E6 | 1.1E8 | 4.4E6 | 2.2E7 |
| (poise) | 1.0 | 2.8E6 | 2.1E7 | 2.8E6 | 8.5E6 |
| | 10 | 1.0E6 | 3.0E6 | 1.1E6 | 1.8E6 |
| | 100 | 2.2E5 | 3.6E5 | 2.3E5 | 2.8E5 |
| TanDel | 0.1 | 2.9 | 0.72 | 3.2 | 1.8 |
| | 1.0 | 1.8 | 0.34 | 1.9 | 0.90 |
| | 10 | 0.86 | 0.17 | 0.90 | 0.44 |

TABLE VI-continued

| Property | Frequ. (rad/sec) | Example 10A | 10B | 10C | 10D |
|---|---|---|---|---|---|
| | 100 | 0.44 | 0.14 | 0.45 | 0.26 |
| Torque | 0.1 | 14.8 | 350 | 13.5 | 67.3 |
| (g-cm) | 1.0 | 86.5 | 663 | 84.5 | 260 |
| | 10 | 325 | 874 | 335 | 573 |
| | 100 | 472 | 624 | 487 | 553 |

EXAMPLES 11–12

In this Example, a condensation catalyst (trifluoroacetic acid) was included in the process of making a silicone pressure-sensitive adhesive composition for use in the devices and method of the present invention along with what was calculated to be approximately a 2:1 ratio of endblocking agent to silicon-bonded hydroxyl content present in the composition before endblocking.

A kettle reactor equipped with a nitrogen sparge tube, ammonia gas sparge tube, agitator, heating coils, thermometer and reflux/overhead condenser was purged with nitrogen and charged with 29 pounds (13.15 kilograms) of PDOS B-1 while a low flow of nitrogen gas was passed through the kettle. 61.9 lbs. (28.08 kg.) of Resin A-1 (67.45% nonvolatile content) was then charged to the reactor followed by 27 lbs. (12.25 kg.) of xylene. The agitator was started and the contents were stirred for one-half hour and then heated to 90°–100° C. A flow of anhydrous ammonia gas was started through the contents at 550 cc/minute and the contents of the reactor was maintained at 90°–100° C. for two hours with ammonia flowing through the contents. After two hours, the ammonia flow was stopped, the reactor contents were cooled to 70° C. and 9 lbs. (4.08 kg.) of hexamethyldisilazane was added to the agitating contents of the reactor followed by a solution of 24.5 g. of trifluoroacetic acid in 1 lb. (0.45 kg.) of xylene. The agitating contents were held for 1 hour with a starting temperature of 68° C. and, at the end of 1 hour, the temperature rose to 80° C. The contents of the reactor were heated to 140° C. and held at reflux for one hour while water was refluxed out of the contents. The contents were held at reflux temperature until the evolution of water had essentially stopped. At that point, solvent was stripped from the contents of the reactor through the overhead condenser until a total of 27 lbs. (12.25 kg.) of solvent was collected. The contents were cooled to 30° C. and 96 lbs. (43.54 kg.) of silicone pressure-sensitive adhesive composition were removed from the reactor. This composition ("Example 11A") had a nonvolatile content of about 59%.

In Example 12, a silicone pressure-sensitive adhesive composition useful in the devices of the present invention was prepared using what was calculated to be about a 2:1 molar ratio of endblocking agent to silicon-bonded hydroxyl radical content of PDOS B-1 and Resin A-1, but without the use of a condensation catalyst. Example 12A was prepared using the following procedure: 244.2 g. PDOS B-1, 522.3 g. Resin A-1 and 229.5 g. xylene are placed in a flask, mixed well and the contents are heated to 100° C. A flow of anhydrous ammonia is sent through the stirring contents (20 cc/minute/2.2 kg. of nonvolatile content) and the contents of the flask is held 2 hours at about 100° C. The nitrogen flow is turned off, the contents are cooled to 80°–90° C. and 82.9 g. hexamethyldisilizane are added to the stirring contents followed by 18 g. of water. The stirring contents are heated to 90°–100° C. and held at that temperature for 3 hours. The contents are then heated to reflux temperature (about 140° C.) and are held at reflux for an additional 3 hours. The contents are then stripped to 70% nonvolatile content using a nitrogen sparge and an overhead condenser to collect solvent being stripped. A composition prepared in this manner was designated as Example 12A.

Samples of Examples 11A and 12A were each evaluated for resistance to diethanolamine as described in Example 10 above. Thus, Examples 11B and 12B were made by adding 2% diethanolamine to the "A" samples and aged for 16 hours at 150° C. as described in Example 10 above. Dynamic Spectrometer data was obtained on each sample after heat aging and the results are reported in Table VII. The testing was done using 1% strain in air at a 30° C. sample temperature.

As can be seen in Table VII, the Dynamic Spectrometer evaluation of control Example 11A and amine-containing Example 11B indicates that the values for G', G", and Eta* are almost identical. Thus, Example 11A is extremely resistant to the effects of the amine which appeared to have the greatest effect observed on the physical properties of the silicone pressure-sensitive adhesives tested. It is expected that this composition will also be analogously resistant to the effects of amino-functional drugs.

Example 12A appeared to have G', G", Eta*, TanDel and Torque values which on an average, were lower than those observed for Example 9A. Referring to the Dynamic Spectrometer values found for Example 10B with 2% diethanolamine, Example 12B with 2% diethanolamine appeared to be affected by the diethanolamine to about the same extent or slightly more than was observed by comparing Example 10A with 10B. It appears that use of the trifluoroacetic acid catalyst improves the ability of the endblocking agent to react with silicon-bonded hydroxyl radicals and thereby its resistance to the effect of amines. Based on the torque values observed for Examples 11A and 12A, the former with the catalyst was a more viscous, more highly cross-linked adhesive. It was also noted that a film of Example 11A was less tacky to the touch than was a film of Example 12A.

TABLE VII

| Property | Frequ. (rad/sec) | Example 11A | 11B | 12A | 12B |
|---|---|---|---|---|---|
| G' | 0.1 | 2.4E6 | 3.4E6 | 1.1E5 | 7.6E6 |
| (d/cm2) | 1.0 | 1.2E7 | 1.4E7 | 9.0E5 | 1.9E7 |
| | 10 | 2.5E7 | 2.7E7 | 5.6E6 | 2.7E7 |
| | 100 | 3.4E7 | 3.5E7 | 1.7E7 | 3.3E7 |
| G" | 0.1 | 3.9E6 | 4.7E6 | 3.2E5 | 5.9E6 |
| (d/cm2) | 1.0 | 8.4E6 | 8.5E6 | 1.7E6 | 6.6E6 |
| | 10 | 7.4E6 | 7.0E6 | 5.6E6 | 5.3E6 |
| | 100 | 6.0E6 | 5.9E6 | 8.9E6 | 5.2E6 |
| Eta* | 0.1 | 4.5E7 | 5.8E7 | 3.4E6 | 9.6E7 |
| (poise) | 1.0 | 1.5E7 | 1.7E7 | 1.9E6 | 2.0E7 |
| | 10 | 2.6E6 | 2.8E6 | 7.9E5 | 2.7E6 |
| | 100 | 3.5E5 | 3.5E5 | 1.9E5 | 3.3E5 |
| TanDel | 0.1 | 1.6 | 1.4 | 2.8 | 0.77 |
| | 1.0 | 0.67 | 0.58 | 1.9 | 0.35 |
| | 10 | 0.29 | 0.26 | 1.0 | 0.20 |
| | 100 | 0.18 | 0.17 | 0.53 | 0.16 |
| Torque | 0.1 | 139 | 178 | 10.3 | 293 |
| (g-cm) | 1.0 | 459 | 515 | 59.2 | 609 |
| | 10 | 794 | 830 | 245 | 810 |
| | 100 | 621 | 634 | 428 | 602 |

EXAMPLE 13

In this Example, samples of the compositions of Examples 7A, 7B and 7D which were stored in sealed jars at room temperature at the start of the aging series described in Example 8 were evaluated using the Dynamic Spectrometer. Each of the control (no drug added) samples had been stored at room temperature for at least one year before the Dynamic Spectrometer data reported for this Example was obtained. For Examples 7A and 7B, the sample containing diethanolamine was made by adding 2% diethanolamine (based on the nonvolatile solids content of the sample) to the aged control sample and put in an aluminum weighing dish in a circulating air oven for 16 hours at 150° C. before Dynamic Spectrometer data was obtained on the heat-aged film for this sample and that of the control. Films of the other samples were cast and the solvent was allowed to evaporate at room temperature before testing.

The remaining samples tested had been in contact with the drug for approximately 10 months at room temperature. No aged control sample for Example 7D was available for testing. The drug-containing samples were run in air at 25° C. sample temperature while the control samples and the diethanolamine-containing samples were run in air at 30° C. A 1% strain setting was used for all samples tested. The results are reported in Table VIII.

From Table VIII, it can be seen that phenylpropanolamine had the least effect on Example 7A. There were somewhat larger effects observed for propranolol and theophylline. Differences in G', G" and Eta* were noted for these drugs, but the changes were not large (i.e., less than one order of magnitude change). Example 7A forms an "aggressive" adhesive film (i.e., is significantly higher in tack than the other adhesive compositions tested in these Examples). It was noted that even though the G', G" and Eta* values for the heat aged film of Example 7A with diethanolamine was more than about an average 1.5 orders of magnitude higher than the heat-aged film prepared from the room temperature-aged sample of Example 7A, the sample containing diethanolamine was still tacky to the touch after exposure to what has been shown to be an amine which has a great effect on the tack value and physical properties of such adhesive compositions. Example 7A is a more aggressive adhesive (prepared with PDOS B-2) and is closer in tack value and properties to comparative Example 6D than to compositions such as Example 7D.

Example 7B had a much less aggressive adhesive character, yet the film from the sample of Example 7B containing diethanolamine was still found to be tacky to the touch even though the value of G' and Eta* relative to the control sample had changed and the torque value also showed a significant change. Propranolol appeared to have slightly less of an effect on Example 7B than did phenylpropanolamine based on the Dynamic Spectrometer data of Table VIII. The phenylpropanolamine-containing sample appeared to have Dynamic Spectrometer property values which were generally less than that of the control and slightly less than those reported for the sample containing propranolol. The same trend was observed for the tack values for these samples reported in Table I.

No control sample was available for Example 7D. The results for Example 7D with phenylpropanolamine may be compared with those obtained for Example 9A with the understanding that the procedures used to prepare each sample were not identical. Relative to control Example 9A, Example 7D after being aged at room temperature in the presence of phenylpropanolamine had higher values of G' but generally lower values of G", Eta* and TanDel. The torque value of Example 7D was generally higher than Example 9A. If it is reasonable to assume that Example 9A is representative of what would be observed for the control sample for Example 7D, the phenylpropanolamine appears to have an effect on Example 7D, but not a large effect.

A review of the 4 month results shown Tables I and II also shows that the properties observed for the control sample of Example 7D were higher than those for the sample with phenylpropanolamine.

TABLE VIII

| Property | Drug/Amine Frequ. (rad/sec) | Example 7A CTRL* | 7A PROPR* | 7A PPA* | 7A THEO* | 7A DEA* | 7B CTRL* | 7B PROPR* | 7B PPA* | 7B DEA* | 7D PPA* |
|---|---|---|---|---|---|---|---|---|---|---|---|
| G' | 0.1 | 1.6E4 | 7.6E3 | 2.7E4 | 4.3E4 | 3.8E6 | 5.9E4 | 1.3E5 | 1.3E5 | 2.4E7 | 5.5E5 |
| (d/cm$^2$) | 1.0 | 1.0E5 | 5.9E5 | 1.3E5 | 1.7E5 | 8.3E6 | 3.4E5 | 5.0E5 | 4.1E5 | 2.9E7 | 3.0E6 |
| | 10 | 3.3E5 | 1.9E5 | 3.1E5 | 4.2E5 | 1.4E7 | 1.9E6 | 1.7E6 | 1.2E6 | 3.3E7 | 9.6E6 |
| | 100 | 8.1E5 | 4.1E5 | 6.4E5 | 1.1E6 | 2.0E7 | 7.6E6 | 5.4E6 | 4.2E6 | 3.6E7 | 1.9E7 |
| G" | 0.1 | 3.4E4 | 1.9E4 | 4.1E4 | 6.1E4 | 2.6E6 | 1.1E5 | 1.6E5 | 1.4E5 | 4.7E6 | 9.3E5 |
| (d/cm$^2$) | 1.0 | 1.1E5 | 6.4E4 | 1.0E5 | 1.4E5 | 3.8E6 | 5.9E5 | 5.4E5 | 3.9E5 | 3.4E6 | 3.2E6 |
| | 10 | 2.7E5 | 1.3E5 | 2.0E5 | 3.4E5 | 4.4E6 | 2.4E6 | 1.7E6 | 1.3E6 | 2.5E6 | 5.8E6 |
| | 100 | 8.6E5 | 3.4E5 | 5.7E5 | 1.2E6 | 5.1E6 | 6.5E6 | 4.4E6 | 4.2E6 | 3.3E6 | 6.9E6 |
| Eta* | 0.1 | 3.7E5 | 2.1E5 | 5.0E5 | 7.4E5 | 4.6E7 | 1.3E6 | 2.1E6 | 1.9E6 | 2.4E8 | 1.1E7 |
| (poise) | 1.0 | 1.5E5 | 8.7E4 | 1.6E5 | 2.2E5 | 9.1E6 | 6.8E5 | 7.4E5 | 5.7E5 | 2.9E7 | 4.4E6 |
| | 10 | 4.3E4 | 2.3E4 | 3.7E4 | 5.4E4 | 1.4E6 | 3.1E5 | 2.4E5 | 1.8E5 | 3.3E6 | 1.1E6 |
| | 100 | 1.2E4 | 5.3E3 | 8.6E3 | 1.6E4 | 2.1E5 | 1.0E5 | 7.0E4 | 5.9E4 | 3.6E5 | 2.0E5 |
| TanDel | 0.1 | 2.2 | 2.5 | 1.5 | 1.4 | 0.69 | 2.0 | 1.2 | 1.1 | 0.20 | 1.7 |
| | 1.0 | 1.1 | 1.1 | 0.80 | 0.82 | 0.46 | 1.8 | 1.1 | 0.93 | 0.12 | 1.1 |
| | 10 | 0.82 | 0.70 | 0.63 | 0.80 | 0.82 | 1.3 | 0.99 | 1.1 | 0.076 | 0.61 |
| | 100 | 1.1 | 0.81 | 0.89 | 1.2 | 0.25 | 0.85 | 0.82 | 1.0 | 0.091 | 0.37 |
| Torque | 0.1 | 1.1 | 0.63 | 1.5 | 2.2 | 140 | 4.0 | 6.4 | 5.8 | 738 | 32.9 |
| (g-cm) | 1.0 | 4.6 | 2.7 | 4.9 | 6.7 | 278 | 20.9 | 22.5 | 17.3 | 891 | 134 |
| | 10 | 13 | 7.2 | 11.4 | 16.6 | 439 | 94.8 | 73.9 | 54.8 | 949 | 350 |
| | 100 | 34 | 15.2 | 24.6 | 45.5 | 441 | 258 | 183 | 159 | 631 | 432 |

*CTRL = Control;
PROPR = Propranolol;
PPA = Phenylpropanolamine;
THEO = Theophylline;
DEA = Diethanolamine

EXAMPLE 14

In this Example, the resistance to diethanolamine of two commercially available silicone pressure-sensitive adhesive compositions was measured using the Dynamic Spectrometer. A sample of the same type of composition as was identified as Example 6A (hereinafter "Example 14A") was mixed with 2% (based on the nonvolatile content of the composition) to produce Example 14B and Example 14D was prepared in the same manner by adding that amount of diethanolamine to a sample of Example 14C. Example 14E was prepared by adding 5% by weight of theophylline (based on the nonvolatile solids content of the composition) to a sample of Example 14C. Small samples of Examples 14A and 14B were placed in aluminum weighing dishes and stored in a circulating air oven for 14 hours at 150° C. Examples 14C, 14D and 14E were placed in weighing dishes and stored in a circulating air oven for 16 hours at 150° C. The physical properties of each of the films taken from the weighing dishes were measured using the Dynamic Spectrometer. All film samples were measured in air at 30° C. The strain setting for Example 14A was 1%; the remaining samples required a strain setting of 10%. The results are reported in Table IX.

Referring to Table IX, the Dynamic Spectrometer values for G', G" and Eta* for Example 14B with diethanolamine have increased dramatically by one to two orders of magnitude relative to the control Example 14A indicating that diethanolamine had a significant effect on this adhesive composition.

Exposure to theophylline (Example 14E) resulted in an increase in G', G" and Eta* values of about one-half order of magnitude which indicates that Example 14C was resistant to the effects of that amino-functional drug. The tack value and viscosity data for Example 6D with theophylline versus the control in Tables I and II appear to confirm this. It was not known by what method this commercially available material was made. Diethanolamine (Example 14D) appeared to have a significant effect on the value of G', G" and Eta* relative to the control Example 14C. The torque value of Example 14D also indicated a significant degree of change relative to control Example 14C.

TABLE IX

| Property | Drug/Amine Frequ. (rad/sec) | Example 14A CTRL* | 14B DEA* | 14C CTRL* | 14D DEA* | 14E THEO* |
|---|---|---|---|---|---|---|
| G' | 0.1 | 1.4E4 | 3.2E6 | 4.4E4 | 3.8E5 | 1.3E5 |
| (d/cm$^2$) | 1.0 | 8.9E4 | 7.2E6 | 1.4E5 | 8.7E5 | 3.1E5 |
| | 10 | 3.8E5 | 1.2E7 | 3.0E5 | 1.5E6 | 7.1E5 |
| | 100 | 1.2E6 | 1.8E7 | 5.4E5 | 2.3E6 | 1.7E6 |
| G" | 0.1 | 3.1E4 | 2.0E6 | 4.6E4 | 3.0E5 | 9.3E4 |
| (d/cm$^2$) | 1.0 | 1.3E5 | 3.2E6 | 8.8E4 | 5.7E5 | 2.1E5 |

TABLE IX-continued

| Property | Drug/Amine Frequ. (rad/sec) | Example 14A CTRL* | 14B DEA* | 14C CTRL* | 14D DEA* | 14E THEO* |
|---|---|---|---|---|---|---|
| | 10 | 4.4E5 | 4.0E6 | 1.5E5 | 8.6E5 | 6.1E5 |
| | 100 | 1.4E6 | 4.8E6 | 3.8E5 | 1.4E6 | 1.9E6 |
| Eta* | 0.1 | 3.4E5 | 3.7E7 | 6.4E5 | 4.9E6 | 1.6E6 |
| (poise) | 1.0 | 1.6E5 | 7.9E6 | 1.7E5 | 1.0E6 | 3.8E5 |
| | 10 | 5.9E4 | 1.3E6 | 3.3E4 | 1.7E5 | 9.4E4 |
| | 100 | 1.8E4 | 1.9E5 | 6.6E3 | 2.7E4 | 2.5E4 |
| TanDel | 0.1 | 2.2 | 0.65 | 1.0 | 0.77 | 0.69 |
| | 1.0 | 1.5 | 0.45 | 0.62 | 0.65 | 0.69 |
| | 10 | 1.2 | 0.32 | 0.51 | 0.58 | 0.86 |
| | 100 | 1.1 | 0.26 | 0.70 | 0.60 | 1.1 |
| Torque | 0.1 | 10 | 114 | 20 | 155 | 51 |
| (g-cm) | 1.0 | 49 | 242 | 52 | 322 | 117 |
| | 10 | 183 | 396 | 104 | 533 | 291 |
| | 100 | 548 | 423 | 201 | 780 | 757 |

*CTRL = Control;
DEA = Diethanolamine;
THEO = Theophylline

That which is claimed is:

1. In a transdermal drug delivery device for the controlled transdermal delivery of a drug comprising a container having a controlled drug delivery means associated therewith, said container being adapted to hold said drug delivery means in close proximity to the skin of a wearer, said device having a biocompatible silicone pressure-sensitive adhesive layer thereon for maintaining contact between said container and the skin of a wearer, the improvement which comprises the combination of an amino-functional drug to be delivered from said drug delivery means and a biocompatible silicone pressure-sensitive adhesive layer which has been deposited from a silicone pressure-sensitive adhesive composition containing silicon-bonded hydroxyl radicals which comprises a combination of (A) from 40 to 70 inclusive parts by weight of at least one benzene-soluble resionous copolymer containing silicon-bonded hydroxyl radicals and consisting essentially of triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer and (B) from 30 to 60 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. where each T is R— or X—, which composition has been chemically treated with at least one chemical treating agent that is reactive to silicon-bonded hydroxyl groups to reduce the silicon-bonded hydroxyl content of the composition to a sufficient degree to thereby render said adhesive layer more resistant to the loss of tack and instant adherence to the skin caused by said amino-functional drug, wherein each R is a monovalent organic radical selected from the group consisting of hydrocarbon radicals of from 1 to 6 inclusive carbon atoms, each X radical is selected from the group consisting of HO—, H— and R'O— radicals, each R' is an alkyl radical of from 1 to 4 inclusive carbon atoms, and each A radical is selected from the group consisting of R— and halohydrocarbon radicals of from 1 to 6 inclusive carbon atoms.

2. The device as claimed in claim 1 wherein [prior to said chemical treatment, the silicone components of the adhesive composition are composed of (A) from 40 to 70 inclusive parts by weight of at least one benzene soluble resin copolymer containing silicon-bonded hydroxyl radicals and consisting essentially of triorganosiloxy units of the formula $R_3SiO_{1/2}$ and tetrafunctional siloxy units of the formula $SiO_{4/2}$ in a mole ratio of 0.6 to 0.9 $R_3SiO_{1/2}$ units for every $SiO_{4/2}$ unit present and (B) from 30 to 60 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. where each T is R— or X—,] said chemical treatment is accomplished by a method which comprises condensing [at least] said (A)[, optionally in the presence of] and (B), with (C) a sufficient amount of *the chemical treatment agent comprising* at least one organosilicon endblocking agent capable of generating an endblocking triorganosilyl unit selected from the group consisting of $ZR_2Si$— units, $CH_3Z'$— units, RZ"— units, and $Z'''R_2Si$— units to provide a 1:0.8 to 1:3 mole ratio of total silicon-bonded hydroxyl radicals present in said (A) and[, when present,] any silicon-bonded hydroxyl and X radicals present in said (B) to total endblocking triorganosilyl units provided by all *organosilicon* endblocking agent present, said *organosilicon endblocking* agent being selected from the group consisting of $ZR_2SiY$, $(ZR_2Si)_qD$, $CH_3Z'Y$, $(CH_3Z')_2O$, RZ"Y' and $(RZ'')_2O$ and $Z'''R_2SiY'$ *wherein said condensing is carried out* at least until a substantial amount of the endblocking triorganosilyl units have reacted with the silicon-bonded hydroxyl radicals of said (A), and [when present,] with the silicon-bonded hydroxyl radicals and X radicals of said (B), wherein each R is a monovalent organic radical selected from the group consisting of hydrocarbon radicals of from 1 to 6 inclusive carbons atoms, each X radical is selected from the group consisting of HO—, [H'] *H*— and R'O— radicals, each R' is an alkyl radical of from 1 to 4 inclusive carbons atoms, each Y radical is a monovalent hydrolyzable organic radical or HO—, each Y' is HO— or a monovalent hydrolyzable organic radical free of nitrogen, each A radical is selected from the group consisting of R— and halohydrocarbon radicals of from 1 to 6 inclusive carbon atoms, each Z radical is A— or QR"—, each R" is a divalent alkylene radical of from 1 to 6 inclusive carbon atoms, each Q is an organofunctional monovalent radical selected from the group consisting of RCOE'—, RE'OC—, NC—, R'E'—, HO—, $G_2N$—, $HO(R''O)_n$—and $G_2NCH_2CH_2NG$—, where E' is —O—, —NG— or —S—, n has a value of from 1 to 6, Z' is

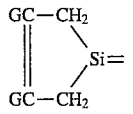

Z" is

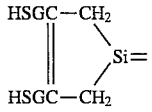

Z''' is selected from the group consisting of HSR"—, $HSCH_2CH_2NGR''$— and $HOCH_2CH_2SR''$— radicals, each G is R— or H—, D is a divalent or trivalent radical capable of being hydrolyzed to release said endblocking silyl unit, q has a value of 2 when D is a divalent radical and q has a value of 3 when D is a trivalent radical, any (B) not having been present when the chemical treatment was made being combined with the endblocked material to complete formation of the silicone portion of said pressure-sensitive adhesive composition.

3. The device of claim 2 wherein the silicone-pressure sensitive adhesive composition is made by the method comprising the steps of (I) mixing said (A), (B), (C)

(D) optionally, an additional catalytic amount of a mild silanol condensation catalyst in the event that none is provided by said (C) *to produce a mixture of (A), (B), (C) and (D) having a viscosity* and (E) when necessary, an effective amount of an organic solvent which is inert with respect to (A), (B), (C) and (D) to reduce the viscosity of a mixture of (A), (B), (C) and (D) and (II) condensing the mixture of (A), (B), (C) and (D) at least until a substantial amount of the endblocking triorganosilyl units have reacted with the silicon-bonded hydroxyl radicals and X radical of said (A) and (B).

4. The device as claimed in claim 3 wherein R is a methyl radical, each said polydiorganosiloxane (B) is composed of ARSiO units selected from the group consisting of $(C_6H_5)_2SiO$, R'''RSiO units and combinations of both where each R''' is selected from the group consisting of methyl, vinyl and 3,3,3-trifluoropropyl radicals and no more than 50 mole percent of the ARSiO units present in said (B) are $(C_6H_5)_2SiO$ units, the endblocking agent of (C) is selected from the group consisting of ZRR''''SiY, $(ZRR''''Si)_2NH$, and mixtures thereof where each Z is R''' and Y is $NH_2$— or R'O—, and each R'''' is a methyl or a phenyl radical, there being present 50 to 65 parts by weight of (A) and 35 to 50 parts by weight of said (B) and [the pKa of the most basis amino-functional radical of] said amino-functional drug [is] *contains an amino-functional radical having a pKa of* at least equal to 8.5.

5. The device as claimed in claim 4 wherein R'''' is methyl radical, all of said ARSiO units in said (B) are $R_2SiO$ units and said (C) is $(R_3Si)_2NH$.

6. The device as claimed in claim 3 wherein said method by which the adhesive composition is made is one wherein Step (I) comprises the steps of (Ia) mixing (A), (B) and any (E) together in the presence of a silanol condensation catalyst, (Ib) condensing said (A) and to form a condensed product and (Ic) mixing the product of Step (Ib) with (C), and (D) and any further amount of (E) which is necessary prior to proceeding with Step (II), said polydiorganosiloxane of (B) having a viscosity of from 100 to 100,000 centipoise at 25° C.

7. The device as claimed in claim 4 wherein said method by which the adhesive composition is made is one wherein Step (I) comprised the Steps of (Ia) mixing (A), (B) and any (E) together in the presence of a silanol condensation catalyst, (Ib) condensing said (A) and (B) to form a condensed product and (Ic) mixing the product of Step (Ib) with (C), any (D) and any further amount of (E) which is necessary prior to proceeding with Step (II), said polydiorganosiloxane of (B) having a viscosity of from 100 to 100,000 centipoise at 25° C.

8. The device as claimed in claim 5 wherein said method by which the adhesive composition is made is one wherein Step (I) comprises the Steps of (Ia) mixing (A), (B) and any (E) together in the presence of a silanol condensation catalyst, (Ib) condensing said (A) and (B) to form a condensed product and (Ic) mixing the product of Step (Ib) with (C), any (D) and any further amount of (E) which is necessary prior to proceeding with Step (II), said polydiorganosiloxane of (B) having a viscosity of from 100 to 100,000 centipoise at 25° C.

9. The device as claimed in claim 2 whereto the pressure sensitive adhesive composition comprises a blend of the chemically treated silicone pressure-sensitive adhesive composition with less than about 30 weight percent based on nonvolatile solids content of a chemically-treated modifier comprising from 1 to 100 parts by weight of a silicone resin copolymer consisting essentially of $R_3SiO_{1/2}$ units and $SiO_{4/2}$ units in a mole ratio of from 0.6 to 0.9 $R_3SiO_{1/2}$ units for each $SiO_{4/2}$ unit present and from 0 to 99 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. wherein the chemical treatment has been made with said endblocking agent (C).

10. The device as claimed in claim 3 wherein said (C) is selected from the group consisting of $ZR_2SiNH_2$, $(ZR_2Si)_2NH$ and mixtures thereof and Q is an organofunctional monovalent radical selected from the group consisting of RCOE'—, RE'OC—, NC—, GE', $HO(R''O)_n$—, where E' is —O—, —NH— or —S—, and said silicone pressure-sensitive adhesive composition is made by a method comprising the steps of (I) mixing (A), (B), (C), (E), (D) and (F) from 0.1 to 10 moles of water per mole of =NH provided by said (C), (G) optionally, from 0.001 to 10 parts by weight per 100 parts by weight of (A) and (B) of at least one ammonia scavenger compound selected from the group consisting of $HOC_mH_{2m+1}$, $HOC_xH_{2x}(OC_xH_{2x})_y(O)_vH$, $C_wH_{2w+1}(OC_xH_{2x-})_yOC_wH_{2w+1}$, $C_wH_{2w+1}$, $C(O)OC_nH_{2n+1}$, $H_2C(O)OC_nH_{2n+1}$, and (II) condensing (A), (B) and (C) at a temperature of from 80° C. to 160° C. and at the same time at least periodically removing any condensation by-products from the mixture at least until a substantial amount of the endblocking triorganosilyl units have reacted with the silicon-bonded hydroxyl radicals and X radicals of said (A) and (B), and (III) stripping substantially any remaining condensation by-products, (F) and any (G) from the mixture after the condensation reaction of step II is substantially complete, wherein m has a value of from 2 to 4, n has a value of from 1 to 6, v is 0 or 1, w has a value of from 1 to 3, x has a value of from 2 to 6 and y has a value of from 0 to 3, there being at least 0.5 moles of water present when (G) is not present.

11. The device as claimed in claim 10 wherein R is a methyl radical, each said polydiorganosiloxane (B) is composed of ARSiO units selected from the group consisting of $(C_6H_5)_2SiO$ R'''RSiO units and combinations of both where each R''' is selected from the group consisting of methyl, vinyl and 3,3,3-trifluoropropyl radicals and no more than 50 mole percent of the ARSiO units present in said (B) are $(C_6H_5)_2SiO$ units, the endblocking agent of (C) is selected from the group consisting of ZRR''''$SiNH_2$, $(ZRR''''Si)_2NH$, and mixtures thereof where each Z is R''' and each R'''' is a methyl or a phenyl radical, there being present 50 to 65 parts by weight of (A) and 35 to 50 parts by weight of said (B) and [the pKa of the most basis amino-functional radical of] said amino-*functional drug* [is] *contains an amino-functional radical having a pKa of* at least 8.5.

12. The device as claimed in claim 11 wherein R'''' is a methyl radical, all of said ARSiO units in said (B) are $R_2SiO$ units and said (C) is $(R_3Si)_2NH$.

13. The device as claimed in claim 10 wherein aid method by which the adhesive composition is made is one wherein Step (I) comprises the steps of (Ia) mixing (A), (B) and any (E) together in the presence of a silanol condensation catalyst, (Ib) condensing said (A) and (B) to form a condensed product and (Ic) mixing the product of Step (Ib) with (C), (F), (G) and any further amount of (E) which is necessary prior to proceeding with Step (II), said polydiorganosiloxane of (B) having a viscosity of from 100 to 100,000 centipoise at 25° C.

14. The device as claimed in claim 11 wherein said method by which the adhesive composition is made is one wherein Step (I) comprised the Steps of (Ia) mixing (A), (B) and any (E) together in the presence of a silanol condensation catalyst, (Ib) condensing said (A) and (B) to form a condensed product and (Ic) mixing the product of Step (Ib) with (C), (F), (G) and any further amount of (E) which is necessary prior to proceeding with Step (II), aid polydiorganosiloxane of (B) having a viscosity of from 100 to 100,000 centipoise at 25° C.

15. The device as claimed in claim 12 wherein said method by which the adhesive composition is made is one wherein Step (F) comprises the Steps of (Ia) mixing (A), (B) and any (E) together in the presence of a silanol condensation catalyst, (Ib) condensing said (A) and (B) to form a condensed product and (Ic) mixing the product of Step (Ib) with (C), (F), (G) and any further amount of (E) which is necessary prior to proceeding with Step (II), said polydiorganosiloxane of (B) having a viscosity of from 100 to 100,000 centipoise at 25° C.

16. The device as claimed in claim 10 wherein Step (I) comprises the steps of (Ia) mixing (A), (B) and any (E) together, (Ib) adding said (C) to the mixture formed in step (Ia) to form a reaction mixture and (Ic) adding said (F) and (G) to the reaction mixture at a preselected point during said Step (II) prior to commencing Step (III).

17. The device as claimed in claim 10 wherein the pressure sensitive adhesive composition comprises a blend of the chemically-treated silicone pressure-sensitive adhesive composition with less than about 30 weight percent based on nonvolatile solids content of a chemically-treated modifier comprising from 1 to 100 parts by weight of a silicone resin copolymer consisting essentially of $R_3SiO_{1/2}$ units and $SiO_{4/2}$ units in a mole ratio of from 0.6 to 0.9 $R_3SiO_{1/2}$ units for each $SiO_{4/2}$ unit present and from 0 to 99 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. wherein the chemical treatment has been made with said endblocking agent (C).

18. The device as claimed in claim 4 wherein there is present from 58 to 65 parts by weight of said (A) and from 35 to 42 parts by weight of said (B).

19. The device as claimed in claim 7 wherein there is present from 58 to 65 parts by weight of said (A) and from 35 to 42 parts by weight of said (B).

20. The device as claimed in claim 3 wherein a catalytic amount of said (D) is present.

21. The device as claimed in claim 5 wherein a catalytic amount of said (D) is present.

22. The device as claimed in claim 10 wherein a catalytic amount of said (D) is present.

23. The device as claimed in claim 12 wherein a catalytic amount of said (D) is present.

24. The device as claimed in claim 2 wherein said (C) is selected from the group consisting of ZRR''''$SiNH_2$, $(ZRR''''Si)_2NH$, and mixtures thereof where each R'''' is a methyl or a phenyl radical and Q is an organofunctional monovalent radical selected from the group consisting of RCOE'—, RE'OC—, NC—, GE', $HO(R''O)_N$—, where E' is —O—, —NH— or —S—, and said silicone pressure-sensitive adhesive composition is made by a method comprising the steps of (I) mixing (A), (B), (C),(E), (D) and (F) from 0.1 to 10 moles of water per mole of =NH provided by said (C), (II) condensing (A), (B) and (C) at a temperature of from 80° C. to 160° C. and at the same time at least periodically removing any condensation by-products from the mixture at least until a substantial amount of the endblocking triorganosilyl units have reacted with the silicon-bonded hydroxyl radicals and x radicals of said (A) and (B), (III) mixing, from 0.001 to 10 parts by weight per 100 parts by weight of (A) and (B) of at least one ammonia scavenger compound selected from the group consisting of $HOC_mH_{2m+1}$, $HOC_xH_{2x}(OC_xH_{2x})_y(O)_vH$, $C_wH_{2w+1}(OC_xH_{2x})_yOC_wH_{2w+1}$, $C_wH_{2w+1}C(O)OC_nH_{2n+1}$, $H_2C(O)OC_{nH2n+1}$, with the product of Step (II), (IV) maintaining the mixture of Step Ill at reflux temperature for a period of time sufficient to improve the removal of residual ammonia present in the mixture of Step III by a stripping step, and (V) stripping substantially any remaining condensation by-products, (F) and (G) from the mixture of Step IV, wherein m has a value of from 2 to 4, n has a value of from 1 to 6, v is 0 or 1, w has a value of from 1 to 3.

25. The device as claimed in claim 24 wherein R'''' is a methyl radical, all of said ARSiO units in said (B) are $R_2SiO$ unit and said (C) is $(R_3Si)_2NH$.

26. The device as claimed in claim 24 wherein said method by which the adhesive composition is made is one wherein Step (I) comprises the steps of (Ia) mixing (A), (B) and any (E) together in the presence of a silanol condensation catalyst, (Ib) condensing said (A) and (B) to form a condensed product and (Ic) mixing the product of Step (Ib)

with (C), (F), and any further amount of (E) which is necessary prior to proceeding with Step (II), said polydiorganosiloxane of (B) having a viscosity of from 100 to 100,000 centipoise at 25° C.

27. A method of preserving the instant adherence to the skin of a wearer of a transdermal drug delivery device for the controlled transdermal delivery of an amino-functional drug wherein said device is maintained in contact with the skin by a skin-contacting silicone pressure-sensitive adhesive layer, said method comprising providing said device with a silicone pressure-sensitive adhesive layer which has been deposited from a silicone pressure-sensitive adhesive composition which consists essentially of a silicone pressure-sensitive adhesive composition containing silicon-bonded hydroxyl radicals which comprises a combination of (A) from 40 to 70 inclusive parts by weight of at least one benzene-soluble resinous copolymer containing silicon-bonded hydroxyl radicals and consisting essentially of triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer and (B) from 30 to 60 parts by weight of at least one polydiorganosiloxane consisting essentially of ARSiO units terminated with endblocking $TRASiO_{1/2}$ units, each polydiorganosiloxane having a viscosity of from 100 centipoise to 30,000,000 centipose at 25° C. where each T is R— or X—, which composition has been chemically treated with at least one chemical treating agent that is reactive to silicon-bonded hydroxyl groups to reduce the silicon-bonded hydroxyl content of the composition to a sufficient degree to thereby render said adhesive layer more resistant to the loss of tack and instant adherence to the skin caused by said amino-functional drug, wherein R is n monovalent organic radical selected from the group consisting of hydrocarbon radicals of from 1 to 6 inclusive atoms, each X radical is selected from the group consisting of HO—, H— and R'O—radicals, each R' is an alkyl radical of from 1 to 4 inclusive carbon atoms, and each A radical is selected from the group consisting of R— and halohydrocarbon radicals of from 1 to 6 inclusive carbon atoms.

28. The method as claimed in claim 27 wherein [prior to said chemical treatment, the silicone components of said adhesive composition are composed of (A) from 40 to 70 inclusive parts by weight of at least one benzene soluble resin copolymer containing silicon-bonded hydroxyl radicals and consisting essentially of triorganosiloxy units of the formula $R_3SiO_{1/2}$ and tetrafunctional siloxy units of the formula $SiO_{4/2}$ in a mole ratio of 0.6 to 0.9 $R_3SiO_{1/2}$ units for every $SiO_{4/2}$ unit present and (B) from 30 to 60 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. where each T is R— or X—,] said chemical treatment is accomplished by a method which comprises condensing [at least] said (A)[, optionally in the presence of] *and* (B), with (C) a sufficient amount of *the chemical treatment agent comprising* at least one organosilicon endblocking agent capable of generating an endblocking triorganosilyl unit selected from the group consisting of $ZR_2Si$— units, $CH_3Z'$— units, RZ" —units, and $Z'''R_2Si$— units to provide a 1:0.8 to 1:3 mole ratio of total silicon-bonded hydroxyl radicals present in said (A) and[, when present,] any silicon-bonded hydroxyl and X radicals present in said (B) to total endblocking triorganosilyl units provided by all *organosilicon* endblocking agent present, said *organosilicon endblocking* agent being selected from the group consisting of $ZR_2SiY$, $(ZR_2Si)_qD$, $CH_3Z'Y$, $(CH_3Z')_2O$, RZ"Y' and $(RZ'')_2O$ and $Z'''R_2SiY'$ at least until a substantial amount of the endblocking triorganosilyl units have reacted with the silicon-bonded hydroxyl radicals of said (A), and [when present,] with the silicon-bonded hydroxyl radicals and X radicals of said (B), wherein each R is a monovalent organic radical selected from the group consisting of hydrocarbon radicals of from 1 to 6 inclusive carbons atoms, each X radical is selected from the group consisting of HO—, H— and R'O— radicals, each R' is an alkyl radical of from 1 to 4 inclusive carbons atoms, each Y radical is a monovalent hydrolyzable organic radical or HO—, each Y' is HO—or a monovalent hydrolyzable organic radical free of nitrogen, each A radical is selected from the group consisting of R— and halohydrocarbon radicals of from 1 to 6 inclusive carbon atoms, each Z radical is A— or QR"—, each R" is a divalent alkylene radical of from 1 to 6 inclusive carbon atoms, each Q is an organofunctional monovalent radical selected from the group consisting of RCOE'—, RE'OC—, NC—, R'E'—, HO—, $G_2N$—, $HO(R''O)_n$—and $G_2NCH_2CH_2NG$—, where E' is —O—, —NG— or —S—, n has a value of from 1 to 6, Z' is

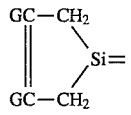

Z' is

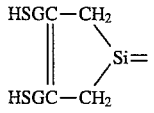

Z''' is selected from the group consisting of HSR"—, $HSCH_2CH_2NGR''$— and $HOCH_2CH_2SR''$— radicals, each G is R— or H—, D is a divalent or trivalent radical capable of being hydrolyzed to release said endblocking silyl unit, q has a value of 2 when D is a divalent radical and q has a value of 3 when D is a trivalent radical, any (B) not having been present when the chemical treatment was made being combined with the endblocked material to complete formation of the silicone portion of said pressure-sensitive adhesive composition.

29. The method as claimed in claim 28 wherein the silicone-pressure sensitive adhesive composition is made by the method comprising the steps of (I) mixing said (A), (B), (C)

(D) optionally, an additional catalytic amount of a mild silanol condensation catalyst in the event that none is provided by said (C) *to produce a mixture of* (*A*), (*B*), (*C*) *and* (*D*) *having a viscosity* and (E) when necessary, an effective amount of an organic solvent which is inert with respect to (A), (B), (C) and (D) to reduce the viscosity of a mixture of (A), (B), (C) and (D) and (II) condensing the mixture of (A), (B), (C) and (D) at least until a substantial amount of the endblocking triorganosilyl units have reacted with the silicon-bonded hydroxyl radicals and X radical of said (A) and (B).

30. The method as claimed in claim 29 wherein R is a methyl radical, each said polydiorganosiloxane (B) is composed of ARSiO units selected from the group consisting of $(C_6H_5)_2SiO$, R'''RSiO units and combinations of both where each R''' is selected from the group consisting of methyl, vinyl and 3,3,3-trifluoropropyl radicals and no more than 50 mole percent of the ARSiO units present in said (B) are $(C_6H_5)_2SiO$ units, the endblocking agent of (C) is selected from the group consisting of ZRR''''SiY, $(ZRR''''Si)_2NH$, and mixtures thereof where each Z is R''' and Y is $NH_2$— or R'O—, and each R'''' is a methyl or a phenyl radical, there being present 50 to 65 parts by weight of (A) and 35 to 50 parts by weight of said (B) and [the pKa of the most basis amino-functional radical of] said amino-functional drug [is] *contains an amino-functional radical having a pKa of* at least equal to 8.5.

31. The method as claimed in claim 30 wherein R'''' is a methyl radical, all of said ARSiO units in said (B) are $R_2SiO$ units and said (C) is $(R_3Si)_2NH$.

32. The method as claimed in claim 29 wherein said method by which the adhesive composition is made is one wherein Step (I) comprises the steps of (Ia) mixing (A), (B) and any (E) together in the presence of a silanol condensation catalyst, (Ib) condensing said (A) and (B) to form a condensed product and (Ic) mixing the product of Step (Ib) with (C), and (D) and any further amount of (E) which is necessary prior to proceeding with Step (II), said polydiorganosiloxane of (B) having a viscosity of from 100 to 100,000 centipoise at 25° C.

33. The method as claimed in claim 30 wherein said method by which the adhesive composition is made is one whereto Step (I) comprises the Steps of (Ia) mixing (A), (B) and any (E) together in the presence of a silanol condensation catalyst, (Ib) condensing said (A) and (B) to form a condensed product and (Ic) mixing the product of Step (Ib) with (C), any (D) and any further amount of (E) which is necessary prior to proceeding with Step (II), said polydiorganosiloxane of (B) having a viscosity of from 100 to 100,000 centipoise at 25° C.

34. The method as claimed in claim 31 wherein said method by which the adhesive composition is made is one whereto Step (I) comprises the Steps of (1a) mixing (A), (B) and any (E) together in the presence of a silanol condensation catalyst, (Ib) condensing said (A) and (B) to form a condensed product and (Ic) mixing the product of Step (Ib) with (C), any (D) and any further amount of (E) which is necessary prior to proceeding with Step (II), said polydiorganosiloxane of (B) having a viscosity of from 100 to 100,000 centipoise at 25° C.

35. The method as claimed in claim 28 wherein the pressure sensitive adhesive composition comprises a blend of the chemically treated silicone pressure-sensitive adhesive composition with less than about 30 weight percent based on nonvolatile solids content of a chemically-treated modifier comprising from 1 to 100 parts by weight of a silicone resin copolymer consisting essentially of $R_3SiO_{1/2}$ units and $SiO_{4/2}$ units in a mole ratio of from 0.6 to 0.9 $R_3SiO_{1/2}$ units for each $SiO_{4/2}$ unit present and from 0 to 99 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. wherein the chemical treatment has been made with said endblocking agent (C).

36. The method as claimed in claim 29 wherein said (C) is selected from the group consisting of $ZR_2SiNH_2$, $(ZR_2Si)_2NH$ and mixtures thereof and Q is an organofunctional monovalent radical selected from the group consisting of RCOE'—, RE'OC—, NC—, GE', $HO(R''O)_n$—, where E' is —O—, —NH— or —S—, and said silicone pressure-sensitive adhesive composition is made by a method comprising the steps of (I) mixing (A), (B), (C), (E), (D) and (F) from 0.1 to 10 moles of water per mole of =NH provided by said (C), (G) optionally, from 0.001 to 10 parts by weight per 100 parts by weight of (A) and (B) of at least one ammonia scavenger compound selected from the group consisting of $HOC_mH_{2m+1}$, $HOC_xH_{2x}(OC_xH_{2x})_y(O)_vH$, $C_wH_{2w+1}(OC_xH_{2x})_yOC_wH_{2w+1}$, $C_wH_{2w+1}C(O)OC_nH_{2n+1}$, $H_2C(O)OC_nH_{2n+1}$, and (II) condensing (A), (B) and (C) at a temperature of from 80° C. to 160° C. and at the same time at least periodically removing any condensation by-products from the mixture at least until a substantial amount of the endblocking triorganosilyl units have reacted with the silicon-bonded hydroxyl radicals and X radicals of said (A) and (B), and (III) stripping substantially any remaining condensation by-products, (F) and any (G) from the mixture after the condensation reaction of step II is substantially complete, wherein m has a value of from 2 to 4, n has a value of from 1 to 6, v is 0 or 1, w has a value of from 1 to 3, x has a value of from 2 to 6 and y has a value of from 0 to 3, there being at least 0.5 moles of water present when (G) is not present.

37. The method as claimed in claim 36 wherein R is a methyl radical, each said polydiorganosiloxane (B) is composed of ARSiO units selected from the group consisting of $(C_6H_5)_2SiO$, R'''RSiO units and combinations of both where each R''' is selected from the group consisting of methyl, vinyl and 3,3,3-trifluoropropyl radicals and no more than 50 mole percent of the ARSiO units present in said (B) are $(C_6H_5)_2SiO$ units, the endblocking agent of (C) is selected from the group consisting of ZRR"41 $SiNH_2$, $(ZRR''''Si)_2NH$, and mixtures thereof where each Z is R''' and each R'''' is a methyl or a phenyl radical, there being present 50 to 65 parts by weight of (A) and 35 to 50 parts by weight of said (B) and [the pKa of the most basis amino-functional radical of] said amino-functional drug [is] *contains an amino-functional radical having a pKa of* at least 8.5.

38. The method as claimed in claim 37 wherein R'''' is a methyl radical, all of said ARSiO units in said (B) are $R_2SiO$ units and said (C) is $(R_3Si)_2NH$.

39. The method as claimed in claim 36 wherein said method by which the adhesive composition is made is one wherein Step (I) comprises the steps of (Ia) mixing (A), (B) and any (E) together in the presence of a silanol condensation catalyst, (Ib) condensing said (A) and (B) to form a condensed product and (Ic) mixing the product of Step (Ib) with (C), (F), (G) and any further amount of (E) which is necessary prior to proceeding with Step (II), said polydiorganosiloxane of (B) having a viscosity of from 100 to 100,000 centipoise at 25° C.

40. The method as claimed in claim 37 wherein said method by which the adhesive composition is made is one wherein Step (I) comprised the Steps of (Ia) mixing (A), (B) and any (E) together in the presence of a silanol condensation catalyst, (Ib) condensing said (A) and (B) to form a condensed product and (Ic) mixing the product of Step (Ib) with (C), (F), (G) and any further amount of (E) which is necessary prior to proceeding with Step (II), said polydiorganosiloxane of (B) having a viscosity of from 100 to 100,000 centipoise at 25° C.

41. The method as claimed in claim 38 wherein said method by which the adhesive composition is made is one wherein Step (I) comprises the Steps of (1a) mixing (A), (B) and any (E) together in the presence of a silanol condensation catalyst, (Ib) condensing said (A) and (B) to form a condensed product and (Ic) mixing the product of Step (Ib) with (C), CF), (G) and any further amount of (E) which is necessary prior to proceeding with Step (II), said polydiorganosiloxane of (B) having a viscosity of from 100 to 100,000 centipoise at 25° C.

42. The method as claimed in claim 36 wherein Step (I) comprises the steps of (1a) mixing (A), (B) and any (E) together, (1b) adding said (C) to the mixture formed in step (1a) to form a reaction mixture and (1c) adding said (F) and (G) to the reaction mixture at a preselected point during said Step (II) prior to commencing Step (III).

43. The method as claimed in claim 36 wherein the pressure sensitive adhesive composition comprises a blend of the chemically-treated silicone pressure-sensitive adhesive composition with less than about 30 weight percent based on nonvolatile solids content of a chemically-treated modifier comprising from 1 to 100 parts by weight of a silicone resin copolymer consisting essentially of $R_3SiO_{1/2}$ units and $SiO_{4/2}$ units in a mole ratio of from 0.6 to 0.9 $R_3SiO_{1/2}$ units for each $SiO_{4/2}$ unit present and from 0 to 99 parts by weight of at least one polydiorganosiloxane consisting essentially of ARSiO units terminated with endblocking $TRASiO_{1/2}$ units, each said polydiorganosiloxane having a viscosity of from 100 centipoise to 30,000,000 centipoise at 25° C. wherein the chemical treatment has been made with said endblocking agent (C).

44. The method as claimed in claim 30 wherein there is present from 58 to 65 parts by weight of said (A) and from 35 to 42 parts by weight of said (B).

45. The method as claimed in claim 33 whereto there is present from 58 to 65 parts by weight of said (A) and from 35 to 42 parts by weight of said (B).

46. The method as claimed in claim 29 wherein a catalytic amount of said (D) is present.

47. The method as claimed in claim 31 wherein a catalytic amount of said (D) is present.

48. The method as claimed in claim 36 wherein a catalytic amount of said (D) is present.

49. The method as claimed in claim 38 wherein a catalytic amount of said (D) is present.

50. The method as claimed in claim 36 wherein said (C) is selected from the group consisting of $ZRR''''SiNH_2$, $(ZRR''''Si)_2NH$, and mixtures thereof where each R'''' is a methyl or a phenyl radical and Q is an organofunctional monovalent radical selected from the group consisting of RCOE'—, RE'OC—, NC—, GE', $HO(R''O)_n$—, where E' is —0—, —NH— or —S—, and said silicone pressure-sensitive adhesive composition is made by a method comprising the steps of (I) mixing (A), (B), (C), (E), (D) and (F) from 0.1 to 10 moles of water per mole of ═NH provided by said (C), (II) condensing (A), (B) and (C) at a temperature of from 80° C. to 160° C. and at the same time at least periodically removing any condensation by-products from the mixture at least until a substantial amount of the endblocking triorganosilyl units have reacted with the silicon-bonded hydroxyl radicals and X radicals of said (A) and (B), (III) mixing, from 0.001 to 10 parts by weight per 100 parts by weight of (A) and (B) of at least one ammonia scavenger compound selected from the group consisting of $HOC_mH_{2m+1}$, $HOC_xH_{2x}(OC_xH_{2x})_y(O)_vH$, $C_wH_{2w+1}(OC_{2x})_yOC_wH_{2w+1}$, $C_wH_{2w+1}C(O)OC_nH_{2n+1}$, $H_2C(O)OC_nH_{2n+1}$, with the product of step (II), (IV) maintaining the mixture of step III at reflux temperature for a period of time sufficient to improve the removal of residual ammonia present in the mixture of step III by a stripping step, and stripping substantially any remaining condensation by-products, (F) and (G) from the mixture of Step IV.

wherein m has a value of from 2 to 4, n has a value of from 1 to 6, v is 0 or 1, w has a value of from 1 to 3.

51. The method as claimed in claim 50 wherein R'''' is a methyl radical, all of said ARSiO units in said (B) are $R_2SiO$ units and said (C) is $(R_3Si)_2NH$.

52. The method as claimed in claim 50 wherein said method by which the adhesive composition is made is one wherein Step (I) comprises the steps of (Ia) mixing (A), (B) and any (E) together in the presence of a silanol condensation catalyst, (Ib) condensing said (A) and (B) to form a condensed product and (Ic) mixing the product of Step (Ib) with (C), (F), and any further amount of (E) which is necessary prior to proceeding with Step (II), said polydiorganosiloxane of (B) having a viscosity of from 100 to 100,000 centipoise at 25° C.

* * * * *